(12) United States Patent
Hallack et al.

(10) Patent No.: US 11,248,774 B2
(45) Date of Patent: Feb. 15, 2022

(54) FLAT PANEL LIGHT MODULE WITH DYNAMIC BEAM

(71) Applicants: Gentex Corporation, Zeeland, MI (US); Mayo Foundation for Medical Education and Research, Rochester, MN (US)

(72) Inventors: Jason D. Hallack, Holland, MI (US); Bradley R. Hamlin, Allendale, MI (US); Todd W. Knallay, Zeeland, MI (US); Danny L. Minikey, Jr., Fenwick, MI (US)

(73) Assignees: GENTEX CORPORATION, Zeeland, MI (US); MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

(21) Appl. No.: 17/070,445

(22) Filed: Oct. 14, 2020

(65) Prior Publication Data
US 2021/0108783 A1 Apr. 15, 2021

Related U.S. Application Data

(60) Provisional application No. 62/956,843, filed on Jan. 3, 2020, provisional application No. 62/915,253, filed on Oct. 15, 2019.

(51) Int. Cl.
*F21V 14/02* (2006.01)
*F21S 8/02* (2006.01)
(Continued)

(52) U.S. Cl.
CPC ............ *F21V 14/025* (2013.01); *F21S 8/026* (2013.01); *F21V 21/049* (2013.01); *F21V 21/26* (2013.01); *F21V 33/0068* (2013.01); *F21W 2131/205* (2013.01); *F21Y 2105/18* (2016.08); *F21Y 2115/10* (2016.08)

(58) Field of Classification Search
CPC ........... F21S 8/026; F21S 2/005; F21V 21/26; F21V 33/0068; F21V 21/049; F21V 23/0471; F21V 21/15; F21V 14/02; F21V 14/30; F21V 21/30; F21W 2131/205;
(Continued)

(56) References Cited

U.S. PATENT DOCUMENTS 4,639,838 A * 1/1987 Kato ...................... F21V 21/30
362/33
5,347,431 A 9/1994 Blackwell et al.
(Continued)

FOREIGN PATENT DOCUMENTS

| WO | 2000035402 | 6/2000 |
|---|---|---|
| WO | 2013111134 A1 | 8/2013 |
| WO | 2019044124 A1 | 3/2019 |

*Primary Examiner* — Peggy A Neils
(74) *Attorney, Agent, or Firm* — Price Heneveld LLP; Brian James Brewer

(57) ABSTRACT

An illumination system includes a light assembly. The light assembly may include a housing having a first zone and a second zone isolated from the first zone. The housing may be configured to fit generally flush with a ceiling. A movable light source may be positioned within the first zone and is configured to emit a first light. A stationary light source may be positioned within the second zone and is configured to emit a second light.

12 Claims, 17 Drawing Sheets

(51) Int. Cl.
*F21V 21/26* (2006.01)
*F21V 33/00* (2006.01)
*F21V 21/04* (2006.01)
*F21W 131/205* (2006.01)
*F21Y 105/18* (2016.01)
*F21Y 115/10* (2016.01)

(58) Field of Classification Search
CPC .............. F21Y 2105/18; F21Y 2115/10; F21Y 2103/20; F21Y 2103/10; A61B 90/30
See application file for complete search history.

(56) References Cited

U.S. PATENT DOCUMENTS

| | | | |
|---|---|---|---|
| 5,564,815 A * | 10/1996 | Littman | F21S 8/028 362/147 |
| 6,079,862 A | 6/2000 | Kawashima et al. | |
| 6,471,363 B1 | 10/2002 | Howell et al. | |
| 7,224,472 B2 | 5/2007 | Bauch et al. | |
| 8,905,585 B2 | 12/2014 | Dallam et al. | |
| 9,119,668 B2 * | 9/2015 | Marka | A61B 1/06 |
| 9,182,092 B2 * | 11/2015 | Cercone | F21S 8/026 |
| 9,222,257 B2 | 12/2015 | Dallam et al. | |
| 10,231,607 B2 | 3/2019 | Charles et al. | |
| 10,240,751 B2 | 3/2019 | Zapata et al. | |
| 10,280,280 B2 * | 5/2019 | Hansen | C08L 33/02 |
| 2010/0214782 A1 * | 8/2010 | Allegri | F21V 21/30 362/249.07 |
| 2010/0315810 A1 * | 12/2010 | Tseng | F21V 14/02 362/234 |
| 2012/0206050 A1 | 8/2012 | Spero | |
| 2015/0308642 A1 * | 10/2015 | Vo | F21V 21/30 362/648 |
| 2017/0038046 A1 * | 2/2017 | Bardot | F21V 21/30 |
| 2017/0180720 A1 | 6/2017 | Jarc | |
| 2019/0060026 A1 | 2/2019 | Geerlings et al. | |
| 2019/0117809 A1 | 4/2019 | Katz | |
| 2019/0282323 A1 | 9/2019 | Petrucci et al. | |

* cited by examiner

FLAT PANEL LIGHT MODULE WITH DYNAMIC BEAM

CROSS-REFERENCE TO RELATED APPLICATIONS

This application claims priority under 35 U.S.C. § 119(e) and the benefit of U.S. Provisional Application Nos. 62/915,253 entitled FLAT PANEL LIGHT MODULE WITH DYNAMIC BEAM, filed on Oct. 15, 2019, by Hallack et al. and 62/956,843 entitled FLAT PANEL LIGHT MODULE WITH DYNAMIC BEAM, filed on Jan. 3, 2020, by Hallack et al., the entire disclosures of which are incorporated herein by reference.

FIELD OF THE DISCLOSURE

The present disclosure generally relates to illumination systems and, more particularly, to dynamic lighting systems.

BACKGROUND OF THE DISCLOSURE

Artificial lighting provided in surgical theaters and medical suites may present a number of issues with regard to positioning, shadows, luminosity, glare and cleaning. Often, medical professionals are not stationary and the lighting needs to be dynamic due to the shifting of personnel and instruments throughout the surgical procedure. Lighting may be suspended from the ceiling in the presence of other medical equipment, such as hoses, monitor stands, booms, imaging equipment, etc. Accordingly, new illumination systems for surgical suites and the like may be advantageous.

SUMMARY OF THE PRESENT DISCLOSURE

According to one aspect of this disclosure, an illumination system is disclosed. The illumination system includes a light assembly. The light assembly includes a housing having a first zone and a second zone isolated from the first zone. The housing is configured to fit generally flush with a ceiling. A movable light source is positioned within the first zone and is configured to emit a first light. A stationary light source including a strip light is positioned within the second zone and is configured to emit a second light.

According to another aspect of this disclosure, a method for controlling an illumination system is disclosed. The illumination system is disposed in a housing configured to fit in an opening of a ceiling and comprising an illumination surface configured to align generally flush with the ceiling. The method includes controlling a projection direction of a movable light source emitted from a central portion of light assembly and controlling ambient lighting from a stationary light source distributed about the central portion. The stationary light source is mechanically disconnected from movement of the movable light source. Controlling the movable light source comprises controlling a first rotation of plurality of rows of lights about a first axis configured to rotate the plurality of rows parallel to the illumination surface and controlling a second rotation of a first row of the plurality of rows of lights about a second axis parallel to the illumination surface. The method may further comprise co-rotating a third rotation of second row of the plurality of rows of lights in connection with the second rotation.

According to yet another aspect of this disclosure, a light assembly is disclosed. The light assembly is disposed in a housing. The housing is configured to fit in an opening of a ceiling and comprising an illumination surface configured to align generally flush with the ceiling. The light assembly comprises a first light module centrally suspended from a frame of the housing. The first light module comprises a first plurality of light sources forming a plurality of rows of lights and a first actuator configured to control a first rotation of the plurality of rows of lights about a first axis. The rotation about the first axis rotates the plurality of rows parallel to the illumination surface. The light assembly further comprises a second light module disposed about the first light module. The second light module is fixedly connected to the housing and emits light through the illumination surface.

These and other aspects, objects, and features of the present disclosure will be understood and appreciated by those skilled in the art upon studying the following specification, claims, and appended drawings. It will also be understood that features of each example disclosed herein may be used in conjunction with, or as a replacement for, features of the other examples.

BRIEF DESCRIPTION OF THE DRAWINGS

The following is a description of the figures in the accompanying drawings. The figures are not necessarily to scale, and certain features and certain views of the figures may be shown exaggerated in scale or in schematic in the interest of clarity and conciseness.

In the drawings.

DETAILED DESCRIPTION

Additional features and advantages of the invention will be set forth in the detailed description which follows and will be apparent to those skilled in the art from the description or recognized by practicing the invention as described in the following description together with the claims and appended drawings.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Figure 1:
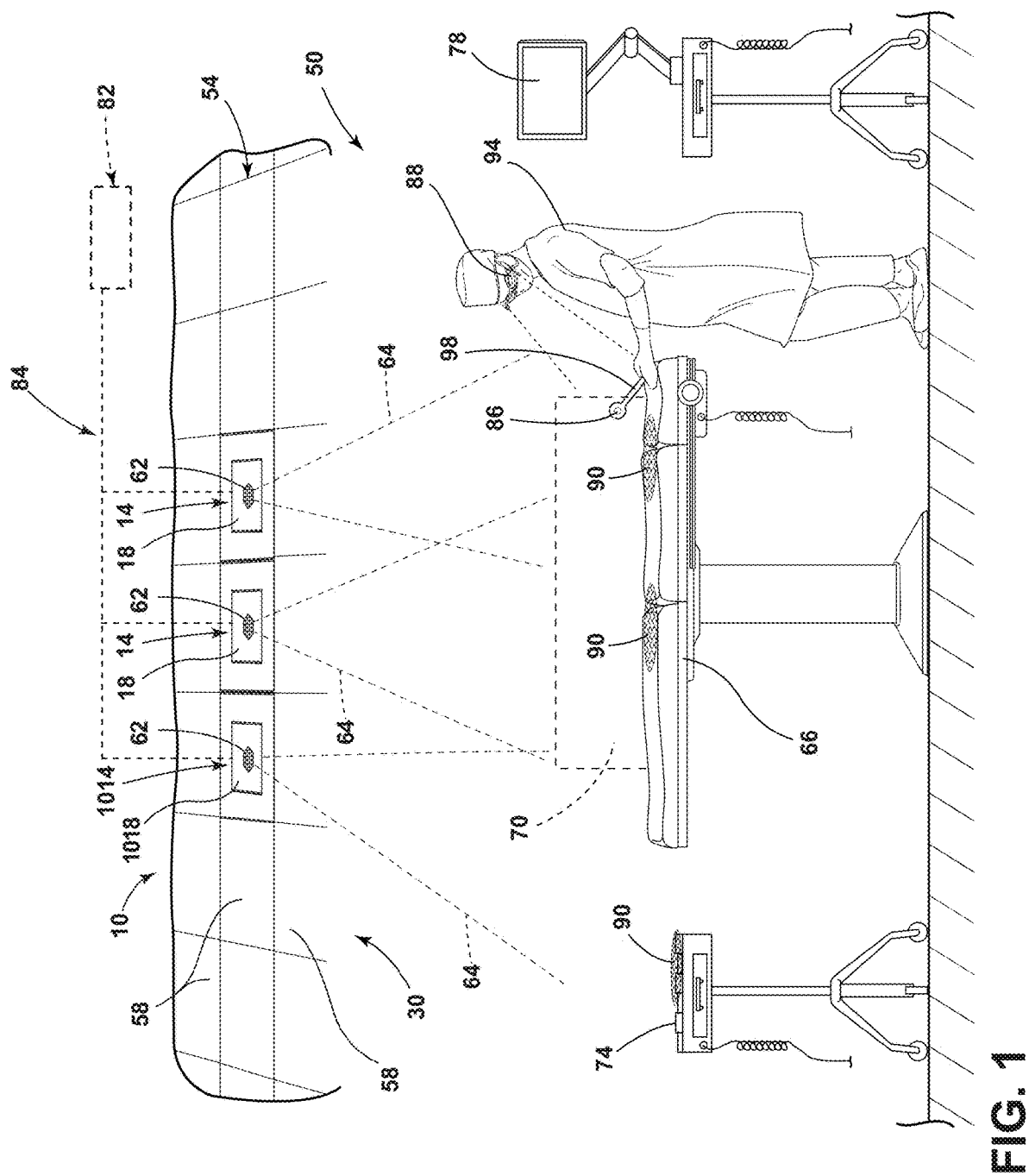
FIG. 1 is a schematic view of a surgical suite comprising an illumination system.
Figure 2A:
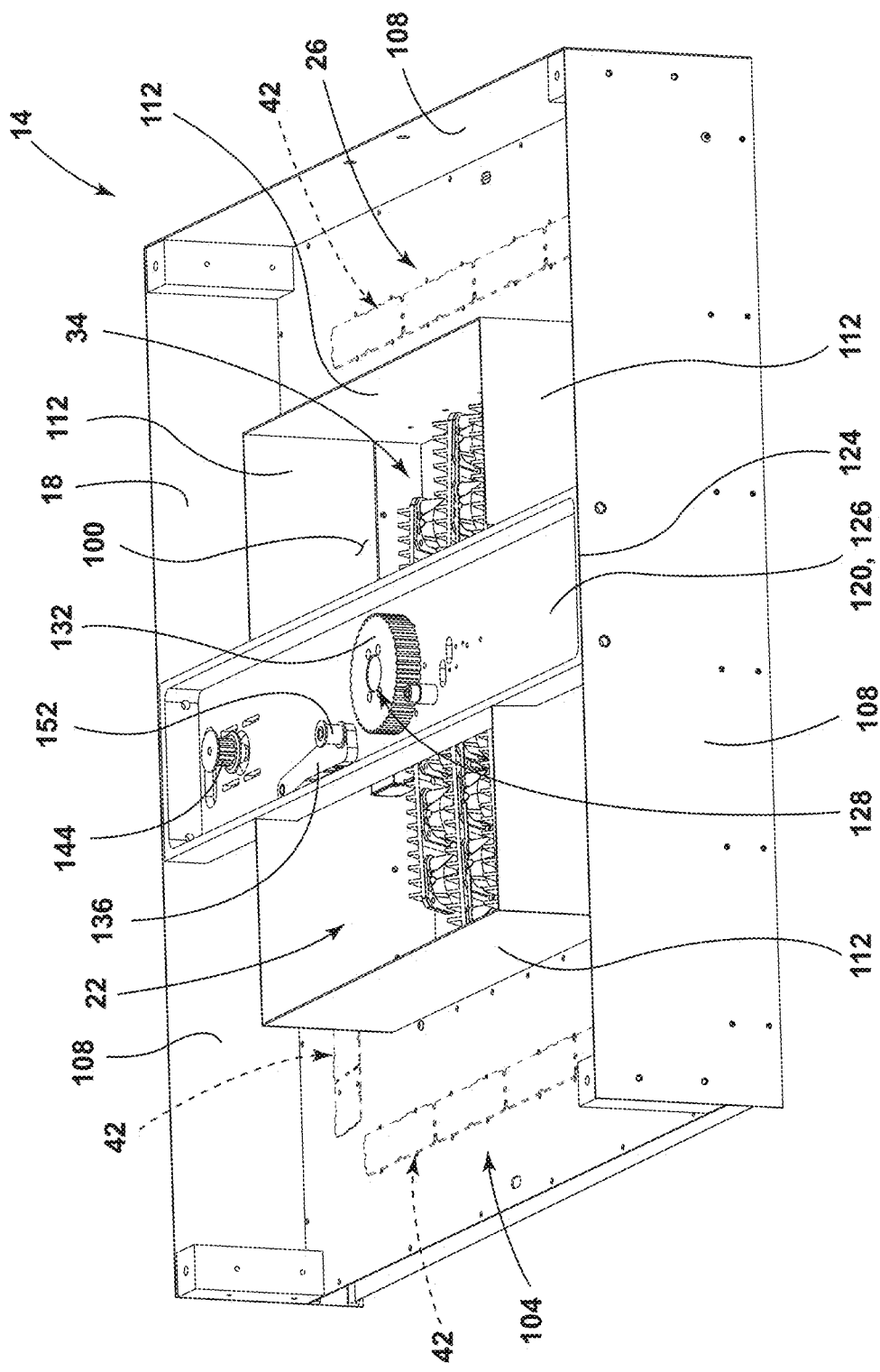
FIG. 2A is a top perspective view of a light assembly according to various aspects described herein.
Figure 8:
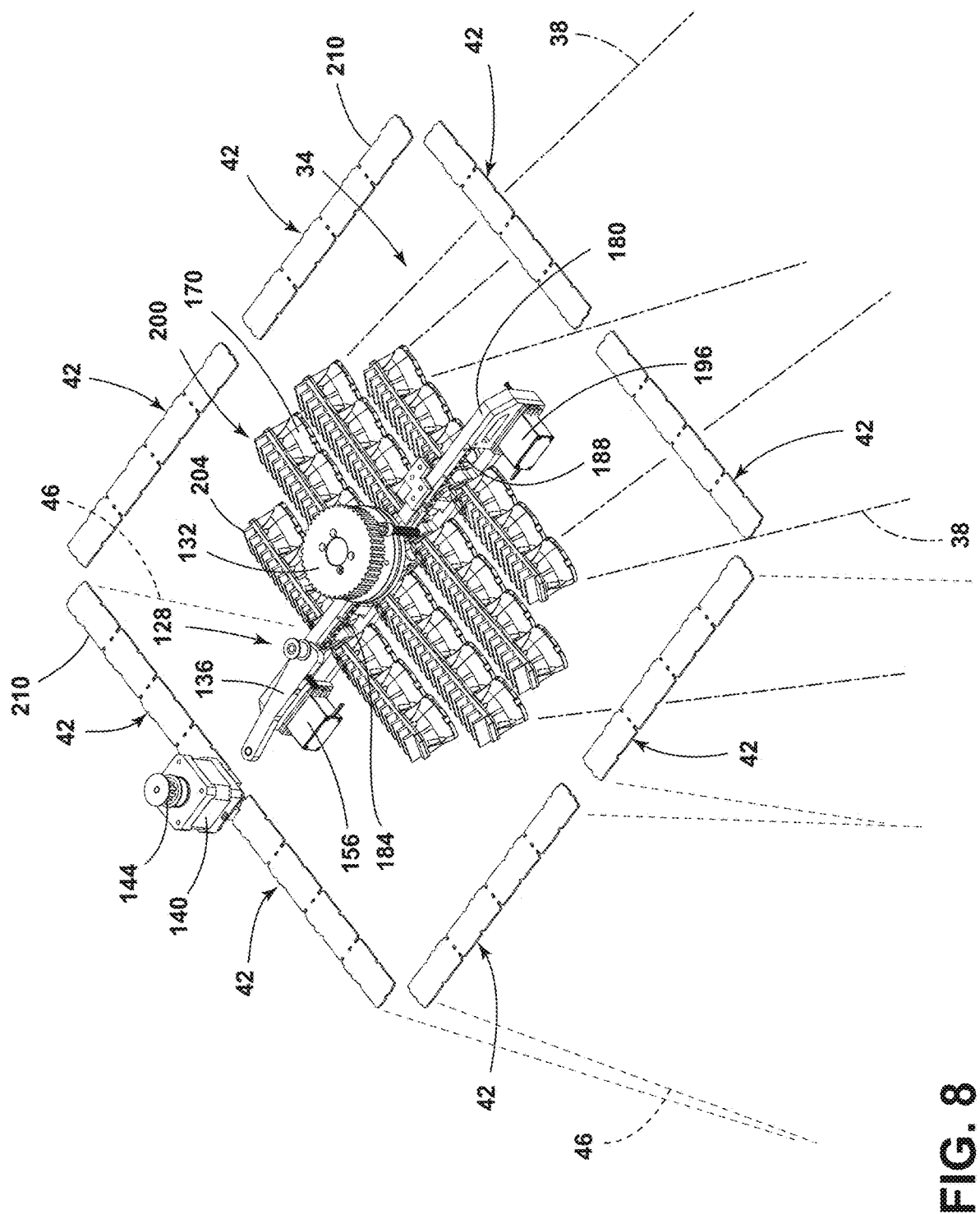
FIG. 8 is a top perspective partial assembly view of the light assembly of FIG. 7.

Referring generally to FIGS. 1, 2A and 8, the disclosure provides for an illumination system 10. The illumination system 10 may include at least one light assembly 14 referred to here as elements 14 and 1014. Though discussed in reference to specific example, it shall be understood that aspects of the light assemblies 14 and 1014 may be implemented in various combinations. As shown in FIG. 2A, the light assembly 14 includes a housing 18, which may include a first zone 22 and a second zone 26 mechanically or structurally isolated from the first zone 22. The housing 18 is configured to fit generally flush with a ceiling 30. A movable light source 34 or first light module is positioned within the first zone 22 and is configured to emit a first light 38. A stationary light source 42 or second light module including a strip light is positioned within the second zone 26 and is configured to emit a second light 46.

Referring now to FIG. 1, the illumination system 10 is depicted in a medical suite 50 and includes one or more of the light assemblies 14 and/or light assemblies 1014. The light assemblies 14, 1014 may take a variety of configurations. In some examples, the light assemblies 14, 1014 may be modular, interconnected, and supported by a drop ceiling grid assembly 54. In this way, the housing 18 may fit generally flush with the ceiling 30 with the housing 18 protruding above the grid assembly 54. For example, the light assemblies 14, 1014 may have rectangular shapes corresponding to the shape of ceiling tiles 58 or openings formed by the grid assembly 54. In specific examples the light assemblies 14, 1014 may include standard dimensions of drop ceiling modules, which may include approximately 2 feet×2 feet (609.6 mm×609.6 mm) or approximately 2 feet×4 feet (609.6 mm×1,219.2 mm). However, it is within the scope of the disclosure for the light assemblies 14, 1014 to include any suitable shape, such as circular, oval, oblong, triangular, square and pentagonal or any polygon shape. It will be understood that different light assemblies 14, 1014 may be provided in different forms and that the illumination system 10 may include a variety of light assemblies 14, 1014. Although described in connection with the medical suite 50, it will be understood that the illumination system 10 of the present disclosure may be utilized in a variety of environments. For example, the illumination system 10 may be utilized in automobile repair areas, doctor's offices, dentistry, photography studios, schools, office buildings, manufacturing settings, movie theaters, retail stores, aircrafts, as well as other areas where dynamic lighting solutions may be advantageous.

The illumination system 10 may include one or more imagers 62 depicted to aid in the use of the illumination system 10. Each of the imagers 62 may be configured to capture image data in a field of view 64 directed into the medical suite 50. In this configuration, the imagers 62 may capture image data, which may be processed by the system 10 to control an emission direction, light intensity, focal length, color temperature or hue, and/or various aspects of the light emitted from the system 10. The imagers 62 may be positioned within or coupled to the light assemblies 14, 1014 (e.g., in the housing 18), a table 66, and/or around the medical suite 50. The imager 62 may be a charge-coupled device (CCD) imager, a complementary metal-oxide-semiconductor (CMOS) imager, other types of imagers, and/or combinations thereof. According to various examples, the imager 62 may include one or more lenses to collimate and/or focus the light reflected by the patient, the table 66, or other features of the medical suite 50.

The table 66 may at least partially define an operating region 70. For the purposes of this disclosure, the operating region 70 may be an operating field which is an isolated area where surgery is performed. The operating region 70 may include furniture and equipment covered with sterile drapes and personnel wearing hygienic uniforms. The table 66 is configured to support a patient during a surgical procedure. According to various examples, the table 66 may have a square, rectangular and/or oval configuration. The table 66 may be configured to tilt, rotate and/or be raised or lowered. In examples where the table 66 is configured to tilt, the table 66 may tilt an angle from approximately 1 degree to approximately 10 degrees about a long or a short axis of the table 66. The tilting of the table 66 may be performed in conjunction with illumination provided from the illumination system 10 and/or the light assemblies 14, 1014. For example, the table 66 may be configured to tilt toward and/or away from the light assemblies 14, 1014 to increase illumination, decrease illumination and/or to eliminate glare reflected from the patient and/or table 66. Further, tilting of the table 66 may be advantageous in allowing users (e.g., medical personnel) positioned around the table 66 to more easily access the patient and/or surgical field. In addition to tilting, it will be understood that the table 66 may be configured to raise or lower, rotate and/or slide about an X-Y plane. Furthermore, the medical suite 50 may include one or more tools or instruments 74 that may be utilized in various procedures and a display screen 78 for viewing information.

In some embodiments, the imagers 62 may capture image data in the fields of view 64 identifying relative lighting (e.g., shadows, reflections, intensity variations, etc.) in medical suite 50 and/or from the operating region 70. The imagers 62 may be configured to relay image data to a controller 82 of the illumination system 10. The controller 82 may include a memory and a processor. The memory may store computer executable commands (e.g., routines) which are controlled by the processor. According to various examples, the memory may include a light control routine and/or an image analyzing routine. The image analyzing routine is configured to process the image data from the one or more imagers 62. For example, the image analyzing routine may be configured to identify shadows and luminosity of the operating region 70, the light from a guidance system 84, location of points of interest (e.g., users around the table 66) and/or gestures from the users.

As discussed herein, the guidance system 84 may correspond to an integrated system comprising the imagers 62 incorporated as integral parts of the system 10 disposed within the housing 18. In such implementations, each of the light assemblies 14 and/or light assemblies 1014 may correspond to self-contained, modular devices that may be utilized in combination to scale the system 10 based on illumination coverage, intensity, dynamic capability (e.g., multiple points of origin to counteract shadows or lighting variation), etc. In some cases, the guidance system 84, which may include one or more of the imagers 62, may be implemented in a separate assembly from the light assemblies 14 and/or light assemblies 1014. In such examples, a processor or controller of the guidance system 84 may be in communication with the controller 82 and communicate lighting information (e.g., the lighting intensity of zones corresponding to coordinates of the medical suite 50 or operating region 70), such that the controller or controllers 82 of the lighting assemblies 14 may illuminate the medical suite 50 or operating region 70 in accordance with a coordinated lighting routine.

According to various examples, the image analyzing routine may also be configured to identify the location of a marker 86 or a wearable device 88 in the image data and to adjust the position of one or more of the movable light sources 34 to one or more target positions 90 in response to the location(s). In some examples, the target positions 90 may be approximately 3 meters from the light assembly 14, 1014. The marker 86 may include a handheld device, wearable device, patch or distinguishable portion of an article of clothing or a glove, which may be handled or worn by personnel in the medical suite 50. The marker 86 may include one or more symbols, computer readable codes and/or patterns which designate a point of interest in the image data. The tracking of the marker 86 may be at least partially determined by the controller 82 of the system 10 by detecting a motion and/or rate of motion of a control instrument 98 comprising the marker 86 identified in the field of view 64, which may include the operating region 70 but is not limited to such. The marker 86 may be disposed on one or more instruments, points of interest in the medical suite 50, and/or the patient.

Once the image analyzing routine has processed the image data from the imager 62, the light control routine may control, move, steer, activate or otherwise influence the light assemblies 14, 1014 to emit light at the location of the marker 86. Such a location may correspond to an area of interest where the user is looking or working (e.g., as measured from the guidance system 84). In this way, the light control routine may steer or otherwise move portions of the first light module formed by one or more of the movable light sources 34 (FIG. 2) to emit a lighting emission to illuminate various areas where the user 94 is looking and/or where hands and instruments may be positioned. In this way, the movable light sources 34 may provide for one of more spotlights.

Alternatively, the user 94 may provide a control input to the illumination system 10 to control, move, steer, activate, adjust, or otherwise influence the light assemblies 14, 1014 to emit light at the location desired by the user 94. Providing input to the illumination system 10 may include utilizing a user interface or control instrument that may be configured to communicate a variety of visual cues to the system 10 to control various settings and operations. Such settings may include, but are not limited to: a control sensitivity, light intensity, light coverage or focus, light color, lighting priority, tracking function, panning and/or control of positioning light sources 34 (FIG. 2), and a variety of configurable settings for the illumination system 10.

The illumination system 10 may further comprise one or more communication circuits, which may be in communication with the controller 82. The communication circuit may be configured to communicate data and control information to a display or user interface, which may include a mobile device, for operating the illumination system 10. Communicating data may include hand gestures, verbal commands, or any suitable method for inputting data to the communication circuit. The user interface may include one or more input or operational elements configured to control the illumination system 10 and communicate data. The communication circuit may further be in communication with more than one of the light assemblies 14, 1014, which may operate in combination as an array of light assemblies 14, 1014. The communication circuit may be configured to communicate via various communication protocols or networks.

In some implementations, the controller 82 may be configured to detect one or more motions, gestures, and/or audio or visual cues identified in the image data captured in the fields of view 64 of the imagers 62 to control the illumination system 10. Exemplary gestures that may be identified by the controller 82 may include a rotation, a lateral motion, an outline (e.g., defining a region of interest, illumination perimeter, etc.) and/or character gesture. In response to detecting each of the gestures, the controller 82 may selectively control one or more settings of the illumination system 10. Such control may be provided in coordination with the operation of the guidance system 84 as discussed herein. The detection of the gestures may be in connection with a movement of the instrument 98, which may be detected by the controller 82 based on a position, orientation, and/or appearance or presence of the markers 86 or symbols identified in the image data captured in one or more of the fields of view 64. The controller 82 may be configured to increase brightness, a proportion or size of an illumination range or region, adjust a color or color temperature, and/or control various operational characteristics of the illumination system 10 in response to detecting each of the gestures.

Referring now to FIG. 2A, the light assemblies 14 of the illumination system 10 may include a first light module comprising one or more of the movable light sources 34 and a second light module comprising the stationary light sources 42. In some examples, the movable light sources 34 are positioned within the first zone 22 and the stationary light sources 42 are fixed and positioned within the second zone 26 of the housing 18. Furthermore, the first zone 22 may be located at a central portion 100 of the housing 18 and may be located within a second zone 26 positioned proximate to a perimeter 104 of the housing 18 or otherwise disposed between the central portion 100 and the housing 18. As shown in FIG. 2A, the second zone 26 may substantially surround or enclose the first zone 22. In such cases, the substantial nature of the stationary light sources 42 may refer to a spacing, separation, or distribution among the individual modules of the stationary light sources that may not continuously surround the central portion 100 and may generally be distributed about the central portion 100. In other words, the stationary light sources 42 may be distributed within the second zone 26, which is disposed between the first zone 22 and the perimeter 104 of the housing 18. The housing 18 may include outer sidewalls 108 and inner sidewalls 112 separating the first zone 22 from the second zone 26 and may be constructed from any suitable material, such as a metal or plastic. Any suitable number of outer and inner sidewalls 108, 112 may be included in the housing 18. In some examples, the outer and inner sidewalls 108, 112 each include four sidewalls defining a rectangular shape. In FIG. 2A, the housing 18 is illustrated without a fourth outer sidewall 108 in order to more clearly demonstrate components of the light assembly 14.

The stationary light sources 42 may be mounted to an underside of a bottom wall 160 of the housing 18 with the use of fasteners and/or adhesives and the like. Thus, the stationary light sources 42 are shown in phantom in FIG. 2A denoting the location on the face of the bottom wall 160 opposing that shown. The bottom wall 160 may be disposed between the outer and inner sidewalls 108, 112. However, the stationary light sources 42 may be positioned within the second zone 26 in any suitable configuration. For example, the stationary light sources 42 may be fixed to any of the outer and inner sidewalls 108, 112.

The movable light sources 34 of the first light module may be coupled to and suspended from a rack 120 positioned at an upper portion 124 of the housing 18. The rack 120 may be in the form of a channel 126 or structural framework, which may be formed of bars, wires, panels, shelves, etc. arranged to support the movable light sources 34. In some examples, the rack 120 extends from one outer sidewall 108 to an opposing outer sidewall 108. In this configuration, the rack 120 may form a bridge extending between the opposing sidewalls 108 and may extend through the inner sidewalls 112 therebetween. In this configuration, the movable light sources 34 forming the central portion 100 of the system 10 may be suspended by the opposing sidewalls 108 of the housing 18, such that the weight associated with the movable light sources 34 and the corresponding gears, motors, or adjustment mechanisms or assemblies may be supported via the grid assembly 54 supporting the perimeter 104 of the housing 18.

The adjustment mechanism of the movable light sources 34 may include a gear system 128 coupled to the rack 120. In the exemplary implementations, the gear system 128 is disposed within and supported by the channel 126 of the rack 120. The gear system 128 may be configured to move or adjust the orientation of the movable light sources 34, which may include panning and tilting. The gear system 128 may include a gear, such as a belt sprocket 132 coupled to the movable light sources 34. The belt sprocket 132 may be configured to rotate at least 360 degrees and up to 540 degrees or as necessary based on a gear ratio of the gear system 128 in order to pan, or swivel the movable light sources 34 over an adjustment range. A sensor housing 136 may be located proximate the belt sprocket 132 and may include magnets and hall sensors configured to determine a rotational position or home position for calibration of the belt sprocket 132. While illustrated as a gear system 128, it is within the scope of the disclosure for the movement of the movable light sources 34 to be controlled via any suitable actuator.

Figure 2B:
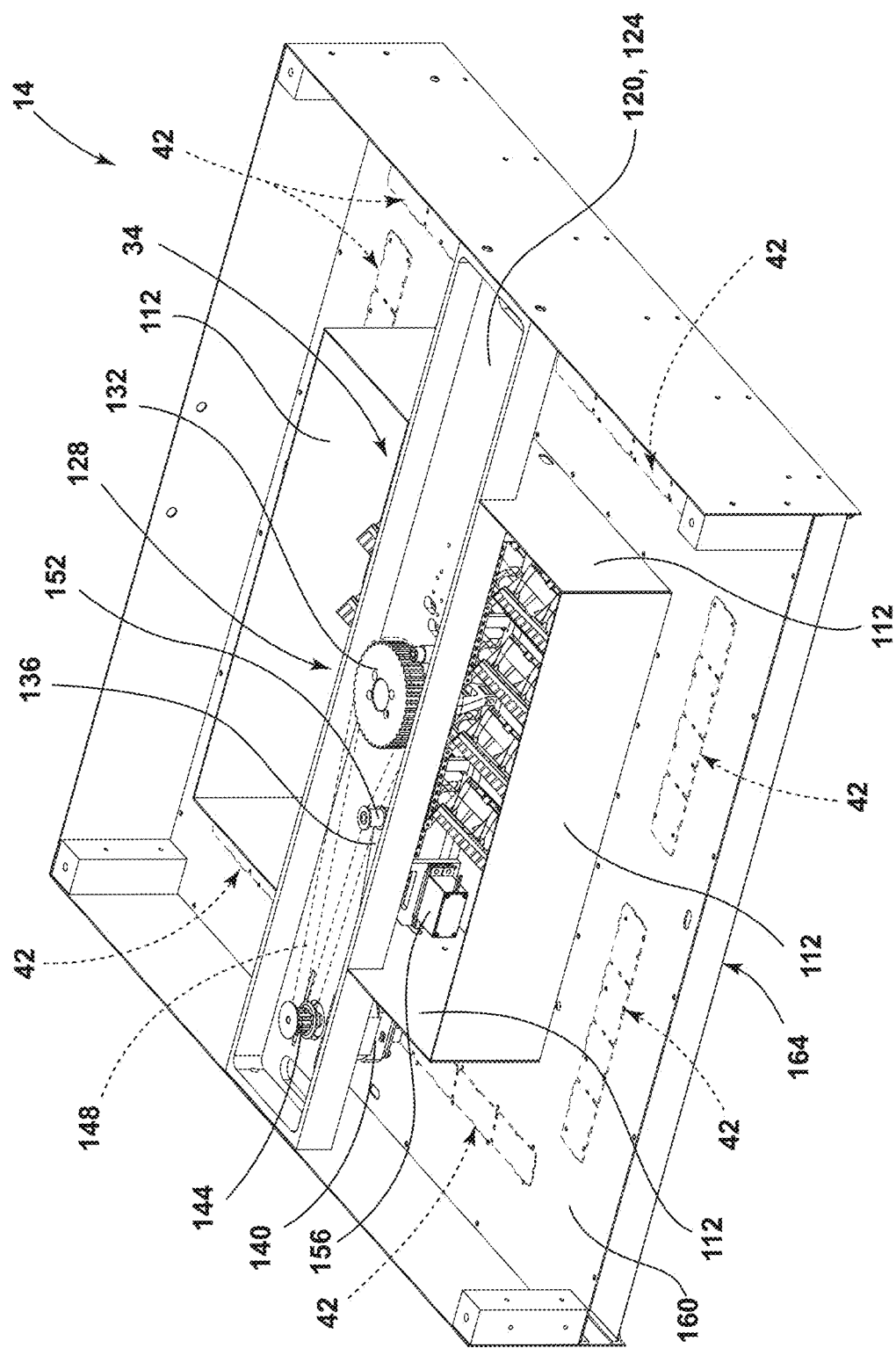
FIG. 2B is a top perspective view of the light assembly of FIG. 2A.

FIG. 2B more clearly illustrates components of the gear system 128. An electrical motor, such as a stepper motor 140, may be provided to control movement of the belt sprocket 132. In some examples, the stepper motor 140 is coupled to the rack 120 and positioned within the second zone 26. The stepper motor 140 may be coupled with an input, such as a drive gear or pulley 144 configured to actuate a rotation of the belt sprocket 132 by applying tension to teeth of a chain or belt 148. The pulley 144 may include a smaller diameter than the belt sprocket 132. However, the diameters of the pulley 144 and the belt sprocket 132 may include any suitable ratio for transmitting a desired rotational output or torque. The chain, or belt 148, may couple the pulley 144 and the belt sprocket 132 to transmit torque. Furthermore, one or more idler pulleys 152 may be provided. In some examples, an idler pulley 152 may be coupled with the sensor housing 136. Optionally, the gear system 128 may include a servo motor 156 configured to control tilting of the movable light sources 34. The servo motor 156 may enable the movable light sources 34 to tilt approximately +/−50 degrees, which will be discussed in more detail with reference to FIG. 5. However, it is within the scope of the disclosure for the stepper motor 140 to control tilting of the movable light sources 34. In such an example, the movable light sources 34 may be coupled to the stepper motor 140 via a rack and pinion configuration. As such, in response to the control signals (e.g., user inputs, guidance system control signals 84, etc.) the controller 82 may control the motor(s) 140 (156) to move, steer, tilt, or otherwise adjust an orientation of the movable light sources 34. It is within the scope of the disclosure for any of the light sources 34, 42 described herein to be fixed or individually articulated. The light sources 34, 42 may all be articulated, a portion may be articulated, or none may be articulated.

Additionally, a windowpane 164 may be disposed exteriorly from the bottom wall 160 and may form a visible surface directed outward into the medical suite 50. The windowpane 164 may be configured to be generally flush with the ceiling tiles 58 (FIG. 1), such that the ceiling 30 may have a planar configuration. As the light assemblies 14 may be positioned in the same geographic space as the ambient lighting, clutter of equipment supported from, or positioned near, the ceiling 30 may be reduced. Furthermore, the windowpane 164 may provide an easily cleanable barrier of movable light sources 34 and the stationary light sources 42 accessible from the outside environment of the medical suite 50.

Figure 3:
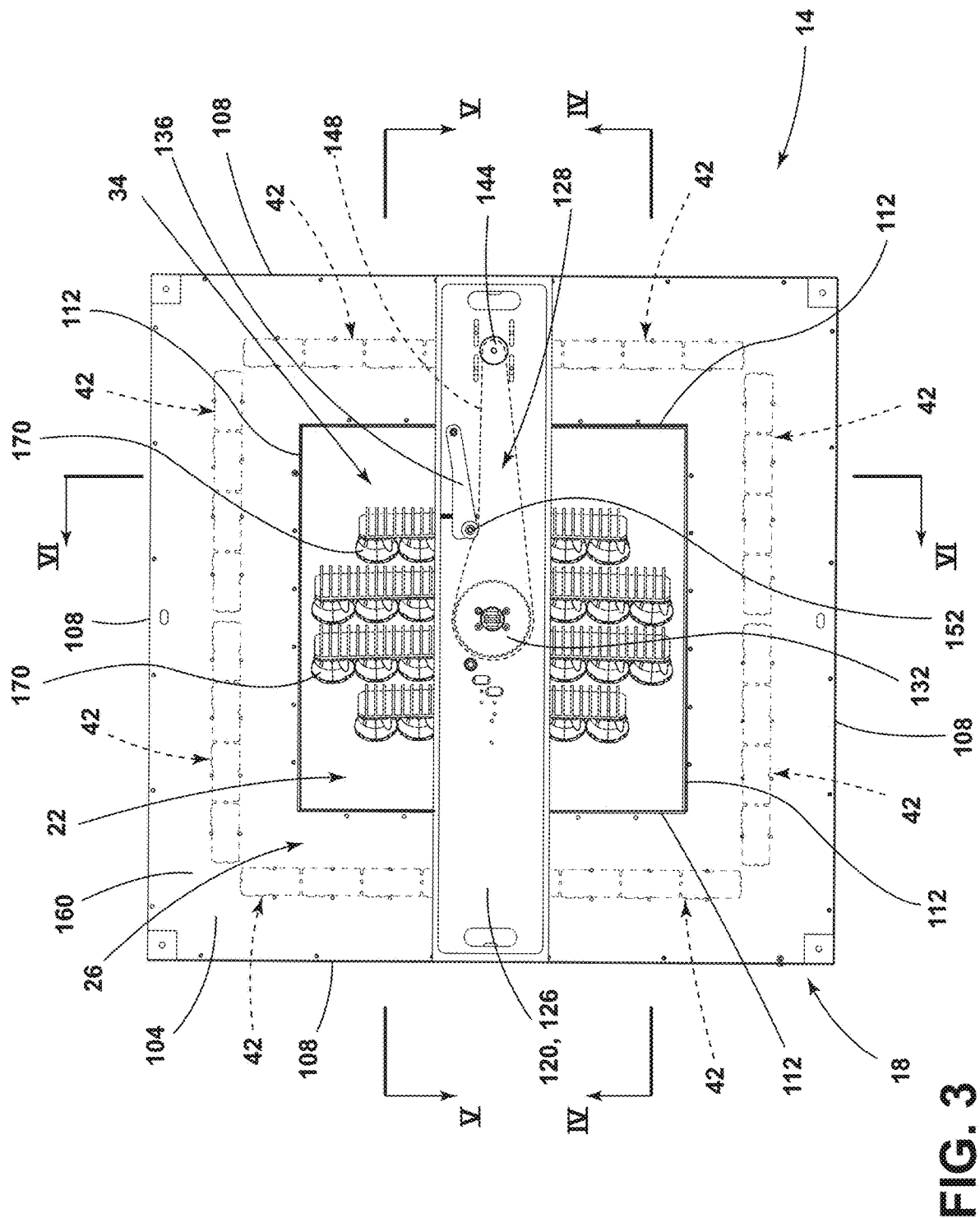
FIG. 3 is a top view of the light assembly of FIG. 2A.

Referring now to FIG. 3, the first zone 22 and the second zone 26 of the light assembly 14 in the housing 18 are more clearly demonstrated. The stationary light sources 42 of the second light module may be mounted to the bottom wall 160 and may substantially surround the movable light sources 34 of the first light module. However, it is within the scope of the disclosure for the first zone 22 and the second zone 26 to include any suitable configuration. For example, the first zone 22 and the second zone 26 may be divided into left and right sides of the housing 18. In another example, one of the first zone 22 and the second zone 26 may form a corner of the housing 18 and the other of the first zone 22 and the second zone 26 may from an L-shape proximate the corner.

The movable light source 34 may be configured as an array of light sources, such as an array of light emitting diode (LED) light sources or LED bulbs 170. In some instances, the LED bulbs 170 include a secondary optic, which may be in the form of a secondary lens configured to generate a pattern of emitted light. An array of LED bulbs 170 may include more than one row, such as four rows of multiple LED bulbs 170. Each row of LED bulbs 170 may include six or eight LED lighting elements. However, it is within the scope of the disclosure for the movable light source 34 to include any suitable configuration or array of LED bulbs 170, which may include more or less than four rows, and more than eight or less than six LED bulbs 170 per row. Alternatively, the movable light source 34 may include a single light source, such as a single LED light source.

Figure 4A:
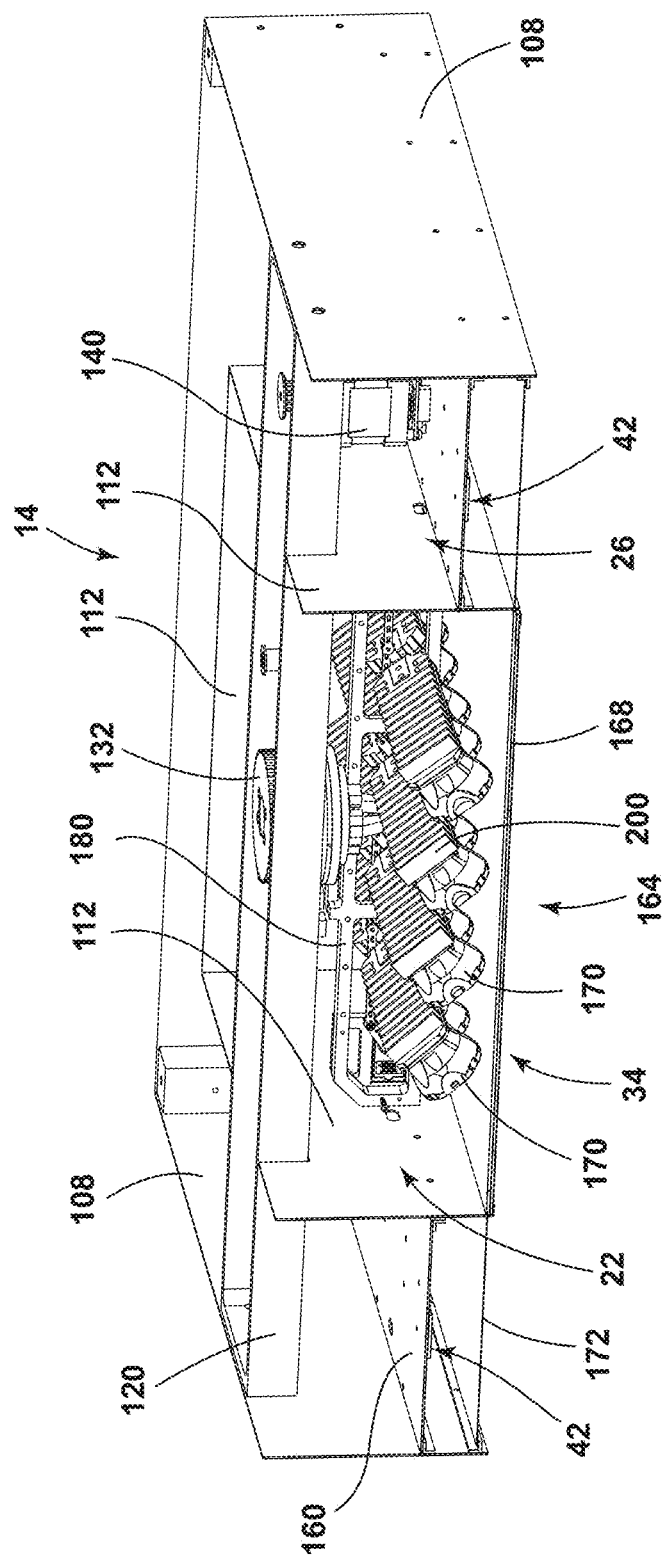
FIG. 4A is a cross-sectional view along line IV-IV of FIG. 3.

FIG. 4A illustrates a perspective cross-section of the light assembly 14 along line IV-IV in FIG. 3 to more clearly illustrate the windowpane 164. As discussed herein, the windowpane 164 may correspond to various forms of light transmissive panels configured to transmit light from the light sources 34, 42 into the medical suite 50. In some examples, the windowpane 164 includes a first windowpane 168 covering the first zone 22 and a second windowpane 172 covering the second zone 26 of the housing 18. The first windowpane 168 and the second windowpane 172 may include any suitable material, which may be substantially transparent. In one example, one or both of the first windowpane 168 and the second windowpane 172 include a laminated safety glass. In another example, one or both of the first windowpane 168 and the second windowpane 172 include an electro-optic element, such as an electrochromic element coupled with at least one substantially transparent substrate. An electrochromic element is configured to vary a transmittance in response to an electrical signal, which may be received from the controller 82. In various implementations, it may be advantageous to include an electrochromic element in one or both of the first windowpane 168 and the second windowpane 172 in order to conceal one or both of the stationary light sources 42 and the movable light sources 34 when not in use.

Figure 4B:
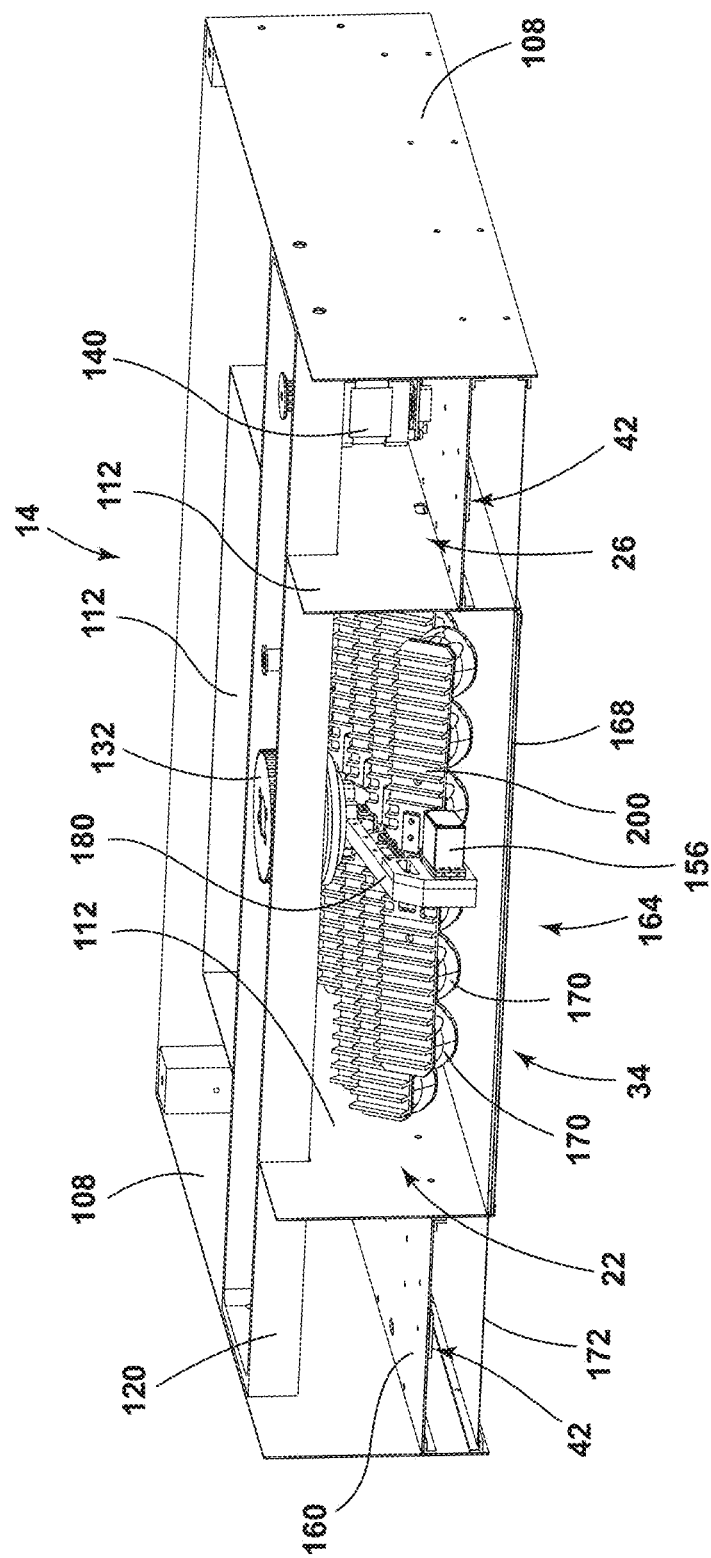
FIG. 4B is the light assembly of FIG. 4A illustrating movable light sources rotated according to various aspects described herein.

FIG. 4B illustrates the light assembly of FIG. 4A where the movable light sources 34 are rotated approximately 90 degrees from the position illustrated in FIG. 4A. As previously discussed, the belt sprocket 132 may be configured to rotate at least 360 degrees and up to 540 degrees or more in order to pan or swivel the movable light sources 34. Additionally, it is within the scope of the disclosure for the controller 82 to control the motor(s) 140 (156) to laterally or vertically move the movable light sources 34 in order to aim emitted light in a desired path.

Additionally, one or both of the first windowpane 168 and the second windowpane 172 may be configured to allow a first handed polarization of light to pass, while eliminating the second handed polarization of light to minimize glare. For example, one or both of the first windowpane 168 and the second windowpane 172 may include an optical filter configured to reflect and/or absorb the second handedness polarization of light. The optical filter may include one or more reflective polarizers and/or absorptive polarizers, which may generally be referred to herein as a polarizer. Reflective polarizer examples may include a wire grid polarizer plus a quarter wave plate or optical retarder, a multilayer plastic film such as a dual brightness enhancement film (DBEF) polarizer with a quarter wave plate, an optical retarder and/or a liquid crystal material. Removal of the second handedness polarization of light may reduce and/or eliminate a perceived glare off of the surgical site, which may affect image data captured by the imagers 62.

Figure 5:
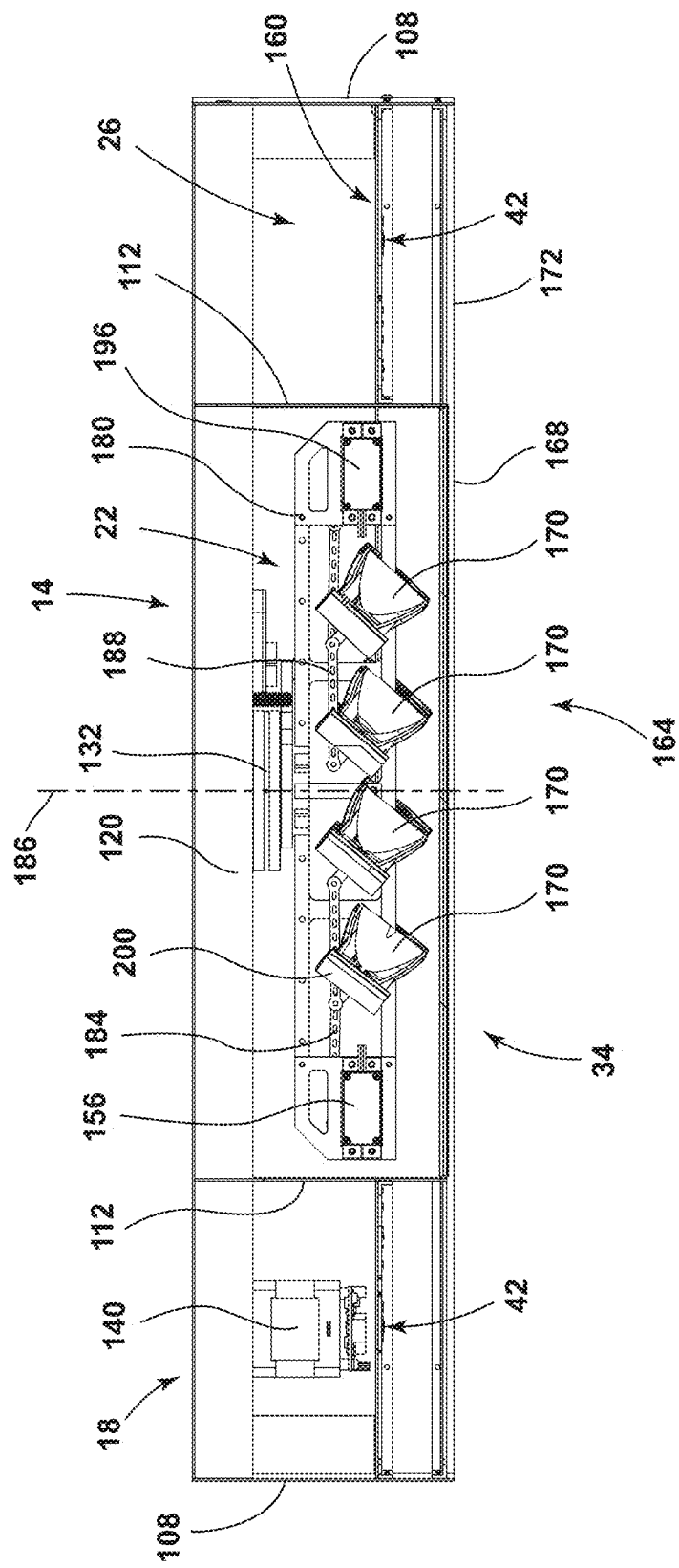
FIG. 5 is a cross-sectional view along line V-V of FIG. 3.

FIG. 5 illustrates a cross-section of the light assembly 14 along line V-V in FIG. 3 to more clearly illustrate an arm 180 configured to retain the movable light sources 34. The arm 180 may be in the form of a framework configured to mount the movable light sources 34 and to operably couple the movable light sources 34 in suspension from the belt sprocket 132 providing for rotation/swiveling about a first rotational axis 186 of the belt sprocket 132. One or more chains coupled with the arm 180, such as a first chain 184 and a second chain 188, may couple with one or more of the rows of the LED bulbs 170. The first chain 184 and the second chain 188 may be operably coupled with electrical motors, such as a first servo motor 156 and a second servo motor 196, respectively. In this way, the first and second servo motors 156, 196 may provide for independent tilting of the movable light sources 34 coupled with the first chain 184 and the second chain 188. Additionally, the corresponding rows of LED bulbs 170 connected to each of the first chain 184 and the second chain 188 may be configured to co-rotate or rotate in linked connection in response to the movement of the first servo motor 156 and a second servo motor 196, respectively. In some examples, the first servo motor 156 and a second servo motor 196 are coupled with the arm 180. However, it is within the scope of the disclosure for a single electrical motor, such as the stepper motor 140, to control all movement of the movable light sources 34 including, but not limited to, swiveling and tilting.

Each of the connected rows of the LED bulbs 170 are shown connected by row supports 198, which may correspond to a heat sink 200. The row supports 198 arrange the LED bulbs 170 or, more generally, the banks of light sources parallel to a second rotational axis 202. In this configuration, each of the row supports 198 and corresponding banks of lights or LED bulbs 170 extends perpendicular to the first rotational axis 186 and parallel to the light transmissive panels or substrates forming the first windowpane 168 covering the first zone 22. That is, each of the row supports 198 may be configured to rotate about axes parallel to the first windowpane 168 or a plane along which the ceiling tiles 58 are supported by the grid assembly 54. In this configuration, each of the row supports 198 is suspended from the belt sprocket 132, such that the row supports 198 rotate together about the first rotational axis 186. Additionally, each of the row supports may be rotated about an axis parallel to the second rotational axis 202 and perpendicular to the first rotational axis 186 as controlled by the servo motors 156, 196. In this configuration, the light assembly 14 provides for multi-axial adjustment of each of the LED bulbs 170 via a novel and economical apparatus.

Referring generally to FIGS. 5-8, the rows of the LED bulbs 170 may be referred to as a first row, a second row, a third row, etc. in order to distinguish among the individual rows as depicted. The movable light sources 34 may be rotated about the first axis by the assemblies discussed herein via the control of a first actuator. Similarly, the rotation of the rows of the LED bulbs 170 about the second axis may be controlled by the servo motors 156, 196, which may also generally be referred to and practiced by one or more actuators (e.g., rotational actuators, stepper motors, etc.). Accordingly, the related operation of the each of the actuators (e.g., stepper motor 140, servo motors 156 and 196, etc.), may generally be discussed herein in reference to the operation, including the independent or otherwise related operation of the actuators to control the rotations about the first axis 186, the second axis 202, and additional related axes (e.g., a third axis of a third row of the LED bulbs 170, a fourth axis of a fourth row of the LED bulbs 170, etc.) to generally describe the related operation of the specifically described exemplary assemblies discussed herein.

Figure 6:
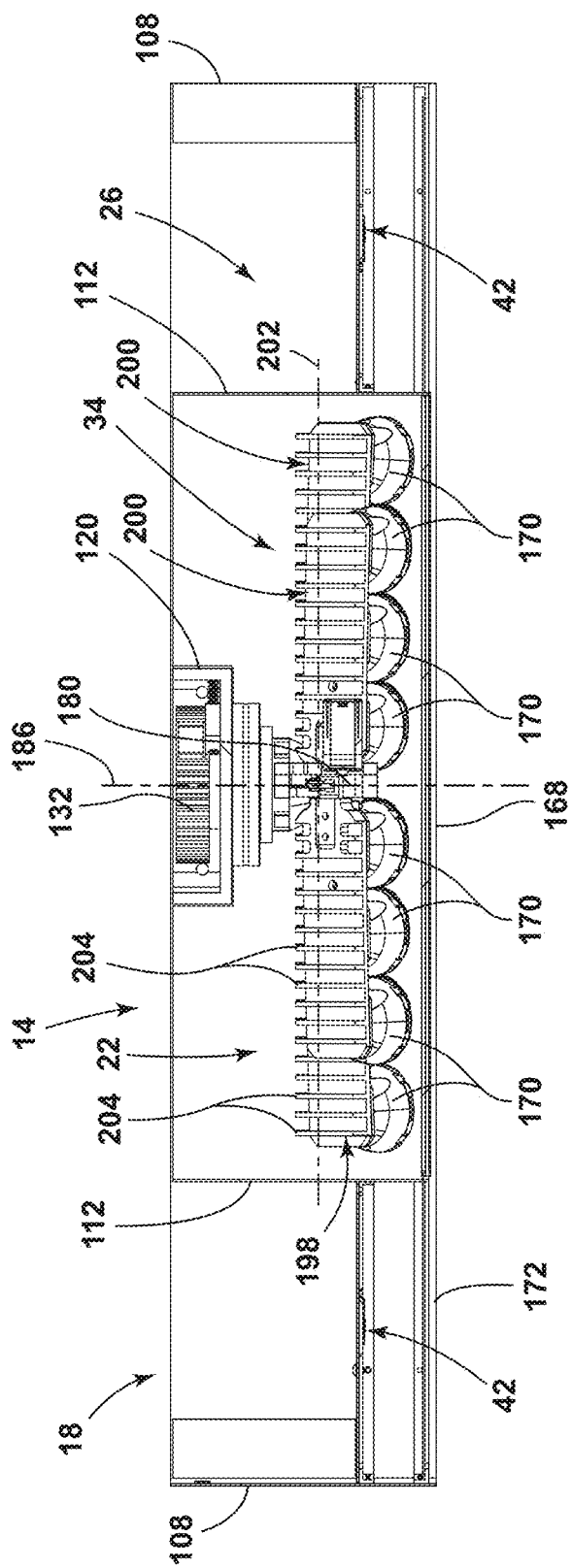
FIG. 6 is a cross-sectional view along line VI-VI of FIG. 3.

Referring now to FIG. 6, a cross-section of the light assembly 14 along line VI-VI in FIG. 3 is illustrated. The movable light sources 34 may be coupled with the arm 180 via board assemblies, which may be in the form of heat sinks 200. The movable light sources 34 may be fastened to the heat sinks 200 with a fastener, such as a screw. Additionally, thermal tape may be used. The heat sinks 200 may include a plurality of vanes 204 to encourage thermal dissipation from the movable light sources 34. The heat sinks 200 may include any suitable material having sufficient thermal conductivity, such as aluminum or copper, but are not limited to such.

Figure 7:
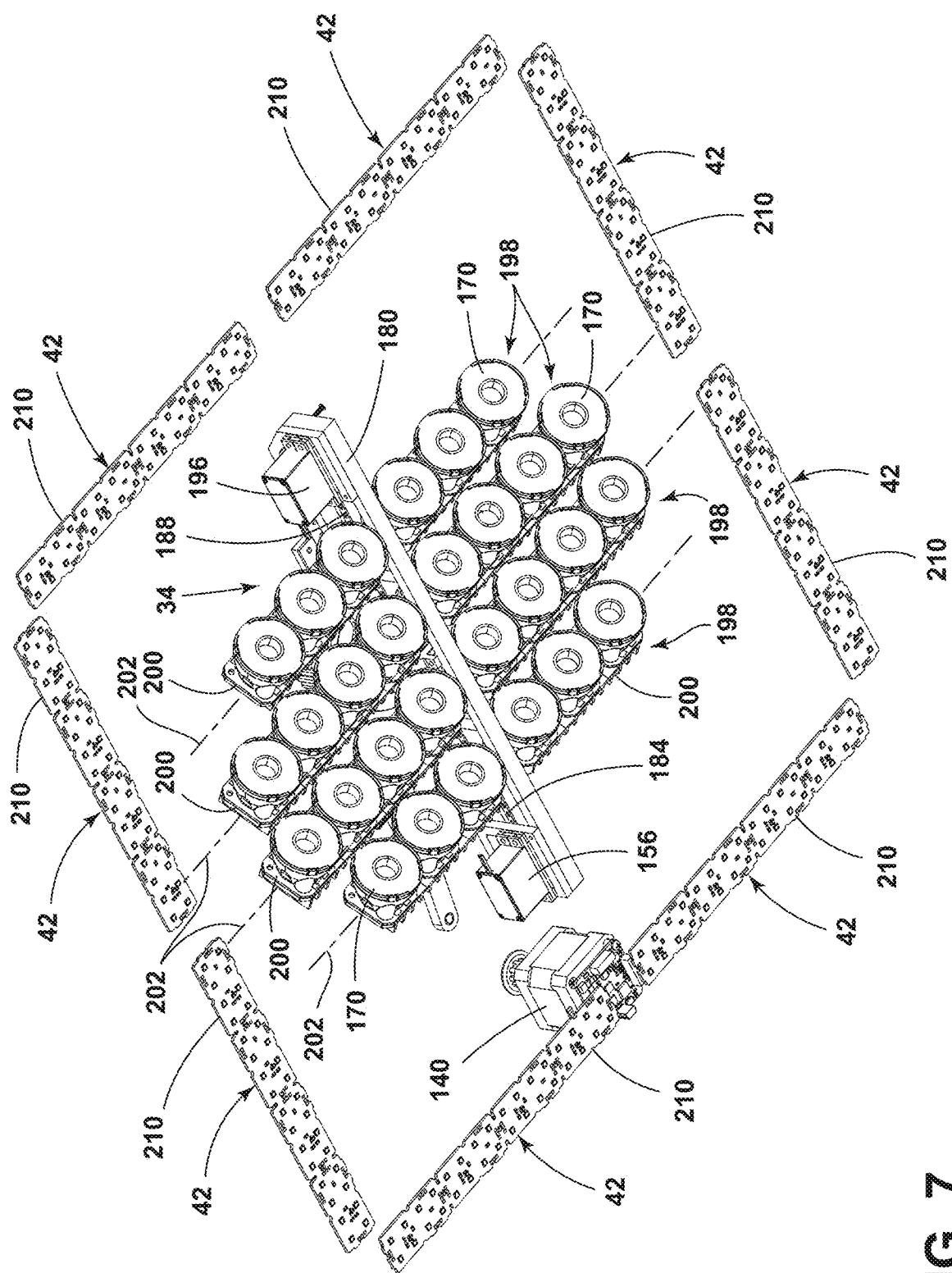
FIG. 7 is a bottom perspective partial assembly view of a light assembly illustrated without a housing according to various aspects described herein.

FIG. 7 illustrates the light assembly 14 without the housing 18 in order to more clearly demonstrate some of the components, such as the stationary light sources 42. The stationary light sources 42 may include a high color rendering index (CRI) LED strip light or array 210. In LED strip light examples of the stationary light sources 42, the strip lights may include surface-mounted devices (SMD), chip on board (COB) devices, multi-COB (MCOB) devices, etc. However, the stationary light sources 42 may be in any suitable form, which may include light bulbs and the like. In some examples, the stationary light sources 42 may be manually adjustable. The stationary light sources 42 may be configured to generate ambient light properties. The movable light sources 34 may include high CRI LEDs having a molded total internal reflection (TIR) lens. The TIR lens may collimate the LED light into efficient, well-controlled light beams. However, the movable light sources 34 may be in any suitable form, which may include light strips and the like. In some examples, the stationary light sources 42 and/or the movable light sources 34 are wired into several different circuits having banks of light sources with varying colors or temperature. String intensity of the stationary light sources 42 may be modulated by the controller 82 to adjust properties including brightness, color, or color temperature, which may include 2700K, 3000K, 6000K, red, orange, green and blue, etc.

As such, the movable light sources 34 and/or the stationary light sources 42 may be configured to emit white light, colored light (e.g., about 390 nm to about 700 nm), infrared light (e.g., about 700 nm to about 1 mm) and/or NIR light (e.g., about 700 nm to about 940 nm or ultraviolet light (e.g. about 10 nm to 400 nm). In various embodiments, the light sources 34, 42 may be configured to produce un-polarized and/or polarized light of one handedness including, but not limited to, certain liquid crystal displays (LCDs), laser diodes, light-emitting diodes (LEDs), incandescent light sources, gas discharge lamps (e.g., xenon, neon, mercury), halogen light sources, and/or organic light-emitting diodes (OLEDs). In polarized light examples of the light sources 34, 42, the light sources 34, 42 are configured to emit a first handedness polarization of light. According to various examples, the first handedness polarization of light may have a circular polarization and/or an elliptical polarization. In electrodynamics, circular polarization of light is a polarization state in which, at each point, the electric field of the light wave has a constant magnitude, but its direction rotates with time at a steady rate in a plane perpendicular to the direction of the wave.

Referring now to FIG. 8, the movable light source 34 may be configured to emit the first light 38 while the stationary light source 42 may be configured to emit the second light 46. In some examples, the first light 38 corresponds to a spotlight, which may be generated by the selectively illuminable LED bulbs 170. The second light 46 may correspond to ambient light, which may be generated by the selectively illuminable LED strip lights 210. In static, or fixed, examples of the stationary light sources 42, the light sources 42 may be directed to focus on various predefined points (e.g., on a patient and/or on the table 66). In some examples, the light assemblies 14 may include reflectors and/or diffusers configured to directionally shift the second light 46.

Figure 9:
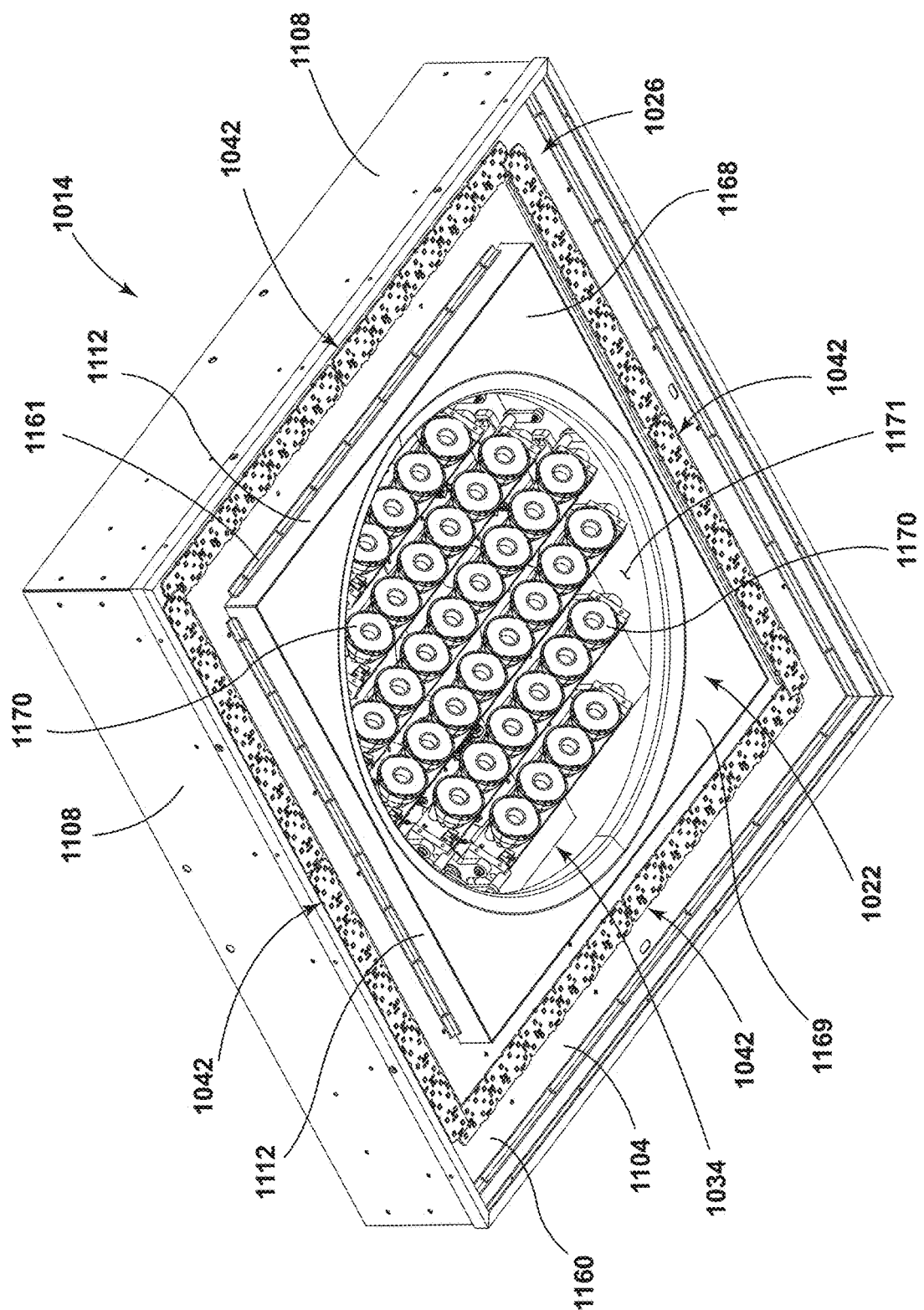
FIG. 9 is a bottom perspective partial assembly view of a light assembly according to various aspects described herein.

Referring now to FIG. 9, the illumination system 10 may include at least one light assembly 1014. The light assembly 1014 is similar to the light assembly 14. Accordingly, similar components will be identified with numerals increasing by 1000, unless identified otherwise. As such, the description with respect to the light assembly 14 applies to the light assembly 1014, unless stated otherwise.

Figure 10:
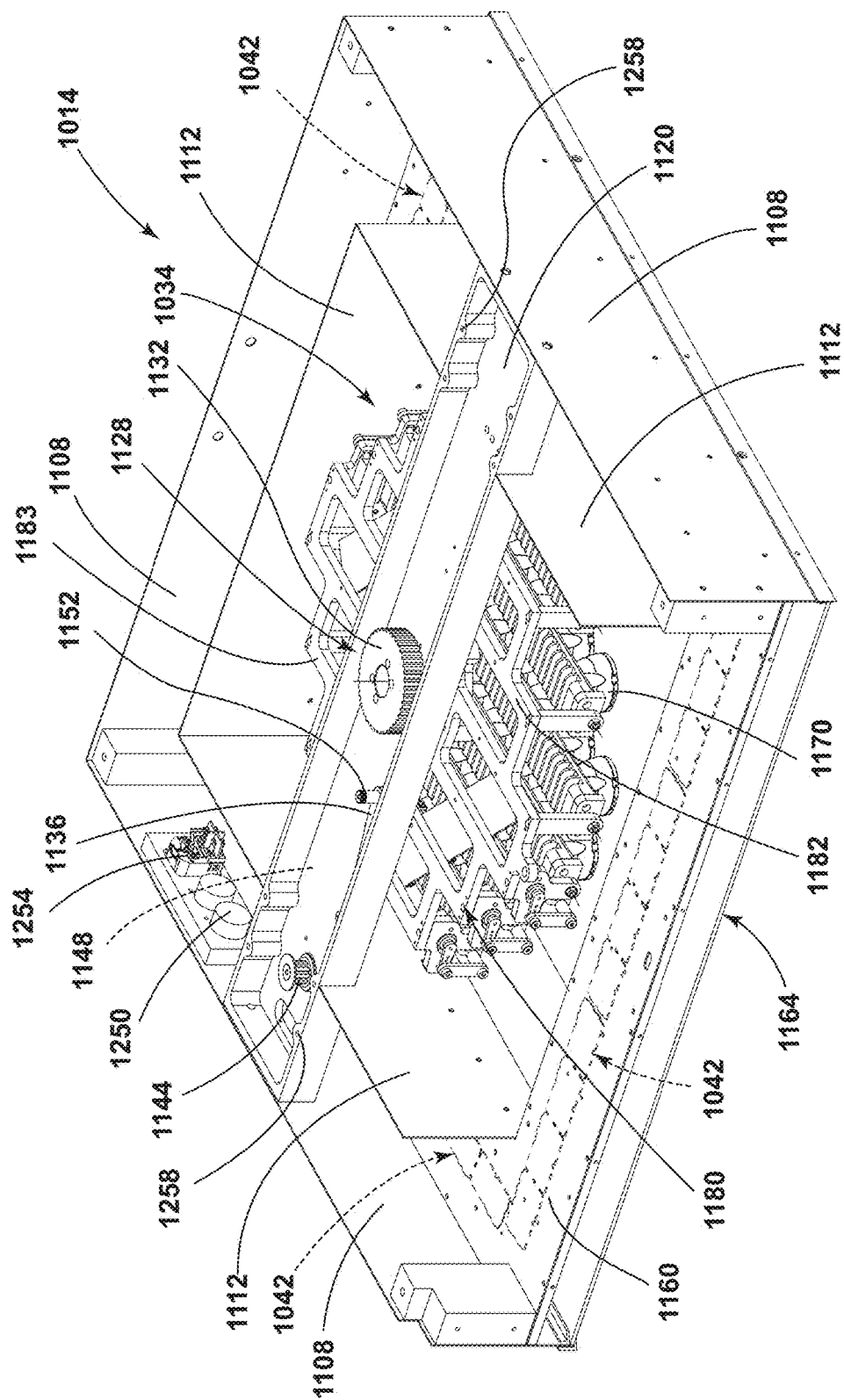
FIG. 10 is a top perspective partial assembly view of the light assembly of FIG. 9 with two of the sidewalls removed.

The light assembly 1014 may include the windowpane 1164 (FIG. 10). Optionally, the light assembly 1014 includes the first windowpane 1168 covering the first zone 1022 and the second windowpane 1172 covering the second zone 1026 located proximate to a perimeter 1104 or forming a perimeter region of the housing 1018. As previously discussed, the light assemblies 1014 may include reflectors and/or diffusers configured to directionally shift light emitted from the stationary light sources 1042. The reflectors and/or diffusers may be operably coupled with the windowpane 1164. Additionally, a polarizing light layer may be coupled with the windowpane 1168.

As illustrated, the first zone 1022 of the housing 1018 may include a closeout panel 1169 defining an aperture 1171 configured to focus light emitted from the movable light sources 1034 of the first light module. The aperture 1171 may be in the form of a circle, oval, square, diamond, etc. The illustrative closeout panel 1169 is coupled to the inner sidewalls 1112 of the housing 1018, which extend through the bottom wall 1160. As illustrated in FIG. 9, the inner sidewalls 1112 may be coupled to the bottom wall 1160 with brackets 1161, but are not limited to such. In some examples, the closeout panel 1169 includes a black anodized material.

Referring now to FIG. 10, the light assembly 1014 is illustrated without one of the inner sidewalls 1112 and the outer sidewalls 1108 to more clearly demonstrate the movable light sources 1034. As previously discussed, the arm 1180 of the movable light sources 1034 is in the form of a framework configured to mount the movable light sources 1034 and to operably couple the movable light sources 1034 to the belt sprocket 1132 for rotation/swiveling. In the illustrative examples, the arm 1180 is in the form of a tilt bracket 1182 configured to operably couple with the rows of LED bulbs 1170. The mounting of the rows of LED bulbs 1170 to the tilt bracket 1182 will be discussed in more detail with respect to FIG. 15.

Similar to the light assembly 14, the assembly 1014 comprises a sensor housing 1136 may be located proximate the belt sprocket 1132 and may include magnets and hall sensors configured to determine a rotational position or home position for calibration of the belt sprocket 1132 and the attached movable light sources 1034. In this configuration, the electrical motor or actuator, such as the stepper motor 1140, may be provided to locate or orient the movable light source 1034 about the first axis 186 (FIGS. 5 and 6). The stepper motor 1140 may be coupled with an input, such as a drive gear or pulley 1144. A chain, or belt 1148, may couple the pulley 1144 and the belt sprocket 1132 to transmit torque. Additionally, one or more idler pulleys 1152 may be provided. In some examples, the idler pulley 1152 may be coupled with the sensor housing 1136. While illustrated as a gear system 1128, it is within the scope of the disclosure for the movement of the movable light sources 1034 to be controlled via any suitable actuator.

Still referring to FIG. 10, the illustrative light assembly 1014 includes a digital multiplex in/out system 1250 and an electrical plug 1254 coupled to an outer sidewall 1108. As a result, a user can easily provide power and digital signals to the light assembly 1014. However, the digital multiplex in/out system 1250 and the electrical plug 1254 may be disposed at any suitable location, including an inner sidewall 1112. Additionally, the rack 1120 may include a plurality of mounting features 1258 configured to receive an end of a handle. As such, when a handle is coupled to the mounting features 1258, a user may easily lift the light assembly 1014 from storage.

Figure 11:
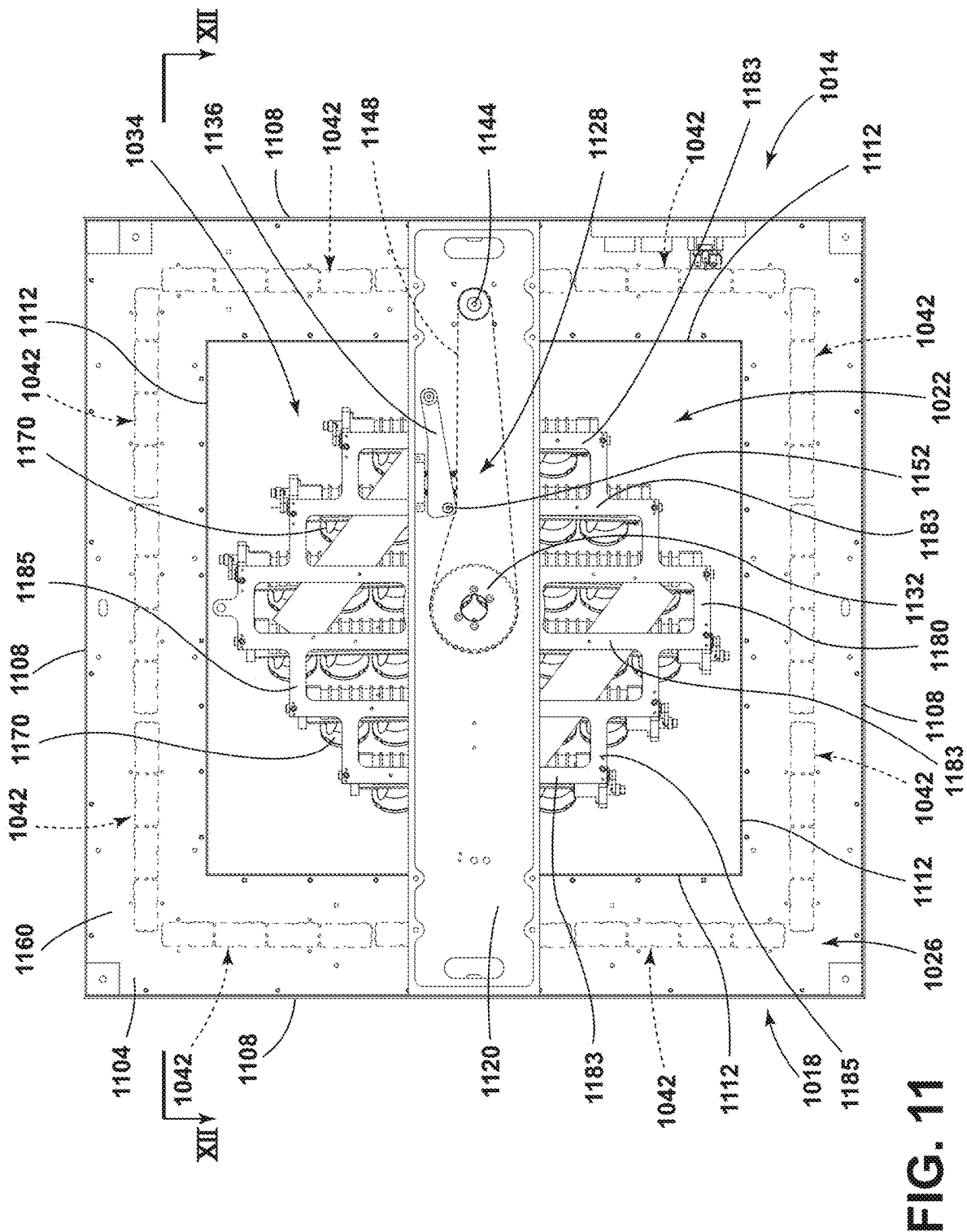
FIG. 11 is a top view of the light assembly of FIG. 9.

Referring now to FIG. 11, the illustrative tilt bracket 1182 includes a plurality of parallel rows 1183 interconnected by transverse segments 1185. The number of rows 1183 may correspond to the number of rows of LED bulbs 1170. In some examples, the length of the rows 1183 corresponds to the length of the rows of LED bulbs 1170. In this way, the tilt bracket 1182 may define a shape corresponding to the array of LED bulbs 1170. For example, the light assembly 1014 may include six rows of LED bulbs 1170 where two center rows of LED bulbs 1170 are the longest and the remaining rows of LED bulbs 1170 gradually decrease in length. As such, the tilt bracket 1182 may include two center rows 1183, which are the longest and the remaining rows 1183 gradually decrease in length.

Figure 12:
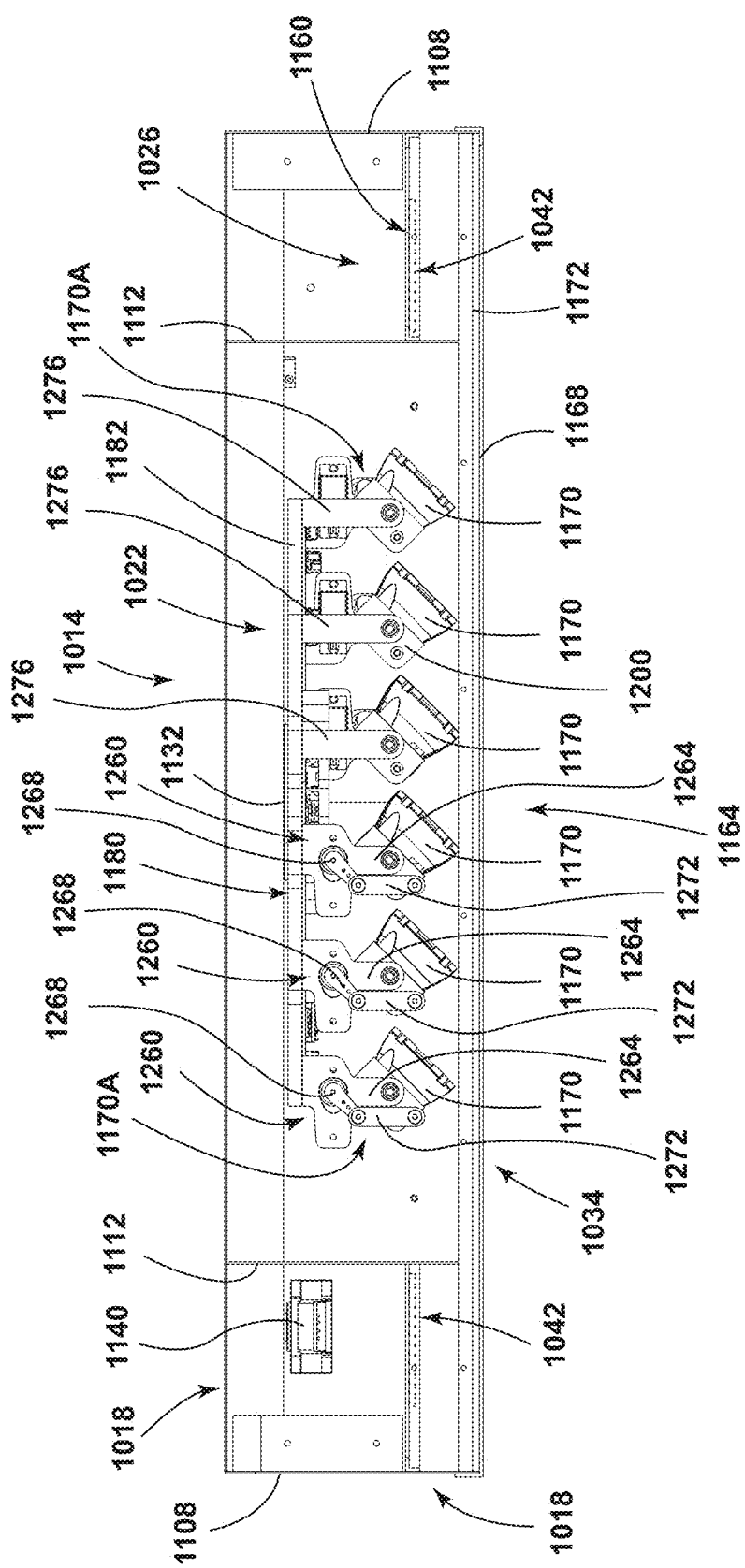
FIG. 12 is a cross-sectional view along line XII-XII of FIG. 11.

FIG. 12 illustrates a cross-section of the light assembly 1014 along line XII-XII in FIG. 11 to more clearly illustrate the rows of LED bulbs 1170 mounted to the tilt bracket 1182. In some aspects, each row of LED bulbs 1170 is independently controlled, such that each row of LED bulbs 1170 can be tilted, or rotated, independently of one another. The rows of LED bulbs 1170 in the illustrative movable light sources 1034 of the first light module are individually controlled by servo motors 1300 (FIG. 15) coupled to an end of the rows of LED bulbs 1170. As previously discussed, the rows of LED bulbs 1170 may be supported by a row supports illustrated in the form of heat sinks 1200. The heat sinks 1200 may include vanes 1204 to encourage thermal dissipation from the movable light sources 1034. The heat sinks 1200 may include any suitable material having sufficient thermal conductivity, such as aluminum or copper, but are not limited to such.

Figure 13:
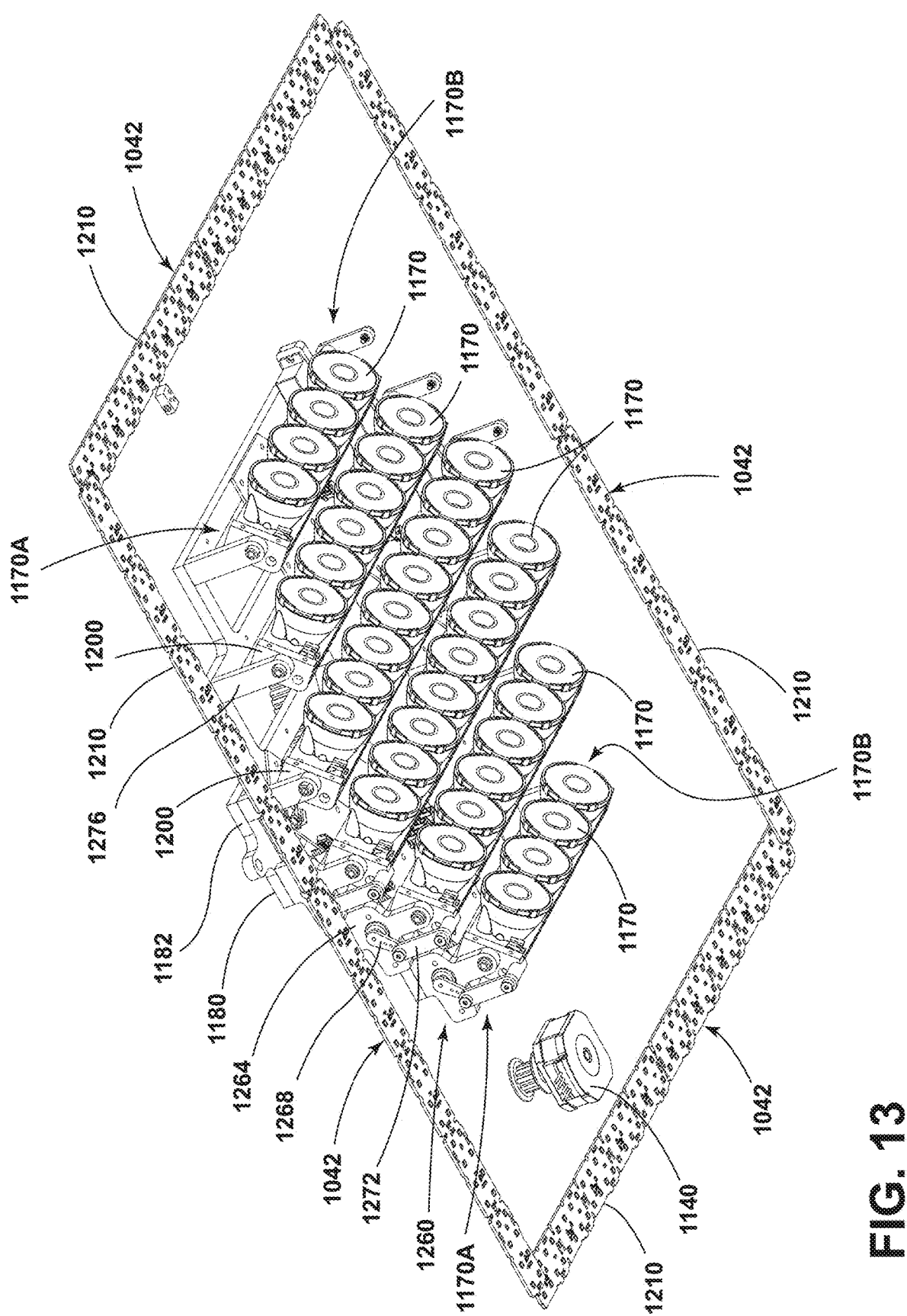
FIG. 13 is a bottom perspective view of a light assembly illustrated without a housing according to various aspects described herein.
Figure 15:
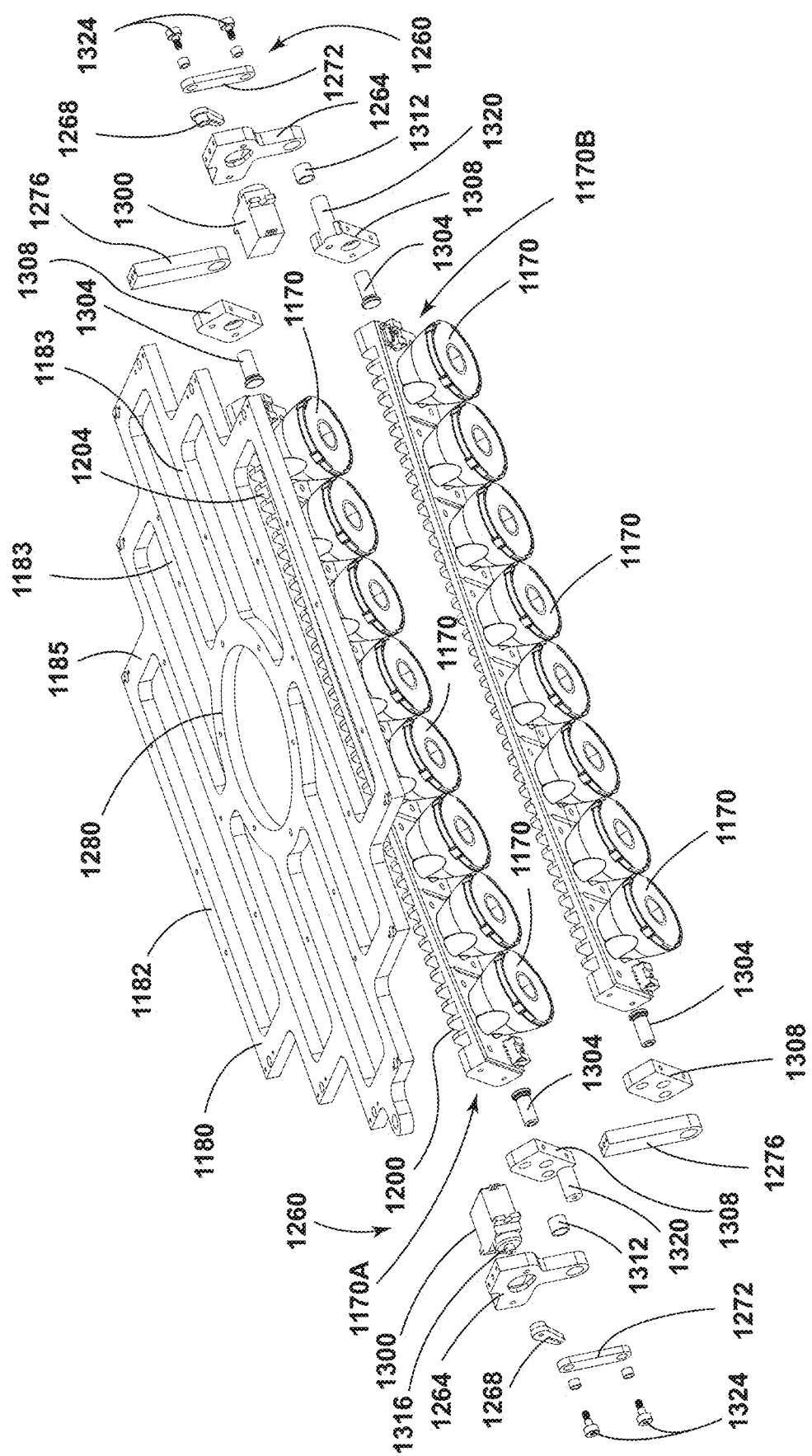
FIG. 15 is a partial exploded view of a movable light source according to various aspects described herein.

The servo motors 1300 are illustrated more clearly with respect to FIG. 15 and may be coupled to either end of the rows of LED bulbs 1170. In some aspects, three of the rows of LED bulbs 1170 include servo couplings 1260 on a first end 1170A and three of the rows of LED bulbs 1170 include the servo couplings 1260 on an opposing, second end 1170B (FIG. 13). The servo couplings 1260 on the second end 1170B (i.e., the right side of the light assembly 1014 depicted in FIG. 12) are hidden behind the rows of LED bulbs and the corresponding support assemblies or row supports as previously discussed herein.

Still referring to FIG. 12, the illustrative servo couplings 1260 include a servo bracket 1264, a servo arm 1268 and a servo linkage 1272. The servo motors 1300 are coupled to the servo bracket 1264, which is also rotatably coupled to the first end 1170A of the row of LED bulbs 1170. The servo bracket 1264 may depend from the tilt bracket 1182. The servo arm 1268 couples the servo bracket 1264 to the servo linkage 1272. The servo linkage 1272 is rotatably coupled to the first end 1170A of the row of LED bulbs 1170.

As shown, the rows of LED bulbs 1170 having servo couplings 1260 on the opposing, second end 1170B (FIG. 13) include drop brackets 1276 on the first end 1170A. The drop brackets 1276 may depend from the tilt bracket 1182 and rotatably couple with the first end 1170A of the row of LED bulbs 1170. The drop brackets 1276 support the row of LED bulbs 1170 while allowing for tilting movement about the second rotational axis 202 as previously discussed in reference to FIGS. 5, 6, and 9. Accordingly, each of the lighting assemblies 14 and 1014 are configured to provide multi-axial rotation about the first rotational axis 186 and the second rotational axis 202 as previously discussed herein.

FIG. 13 demonstrates the light assembly 1014 without the housing 1018 to clearly demonstrate some of the components, such as the stationary light sources 1042 of the second light module. As previously discussed, the stationary light sources 1042 may include a high color rendering index (CRI) LED strip light or array 1210. In LED strip light examples of the stationary light sources 1042, the strip lights may include surface-mounted devices (SMD), chip on board (COB) devices, multi-COB (MCOB) devices, etc. Additionally, the first end 1170A of the rows of LED bulbs 1170 and the opposing, second end 1170B can be seem more clearly. Furthermore, the LED bulbs 1170 may include a secondary optic, which may be in the form of a secondary lens configured to generate a pattern of emitted light.

Figure 14:
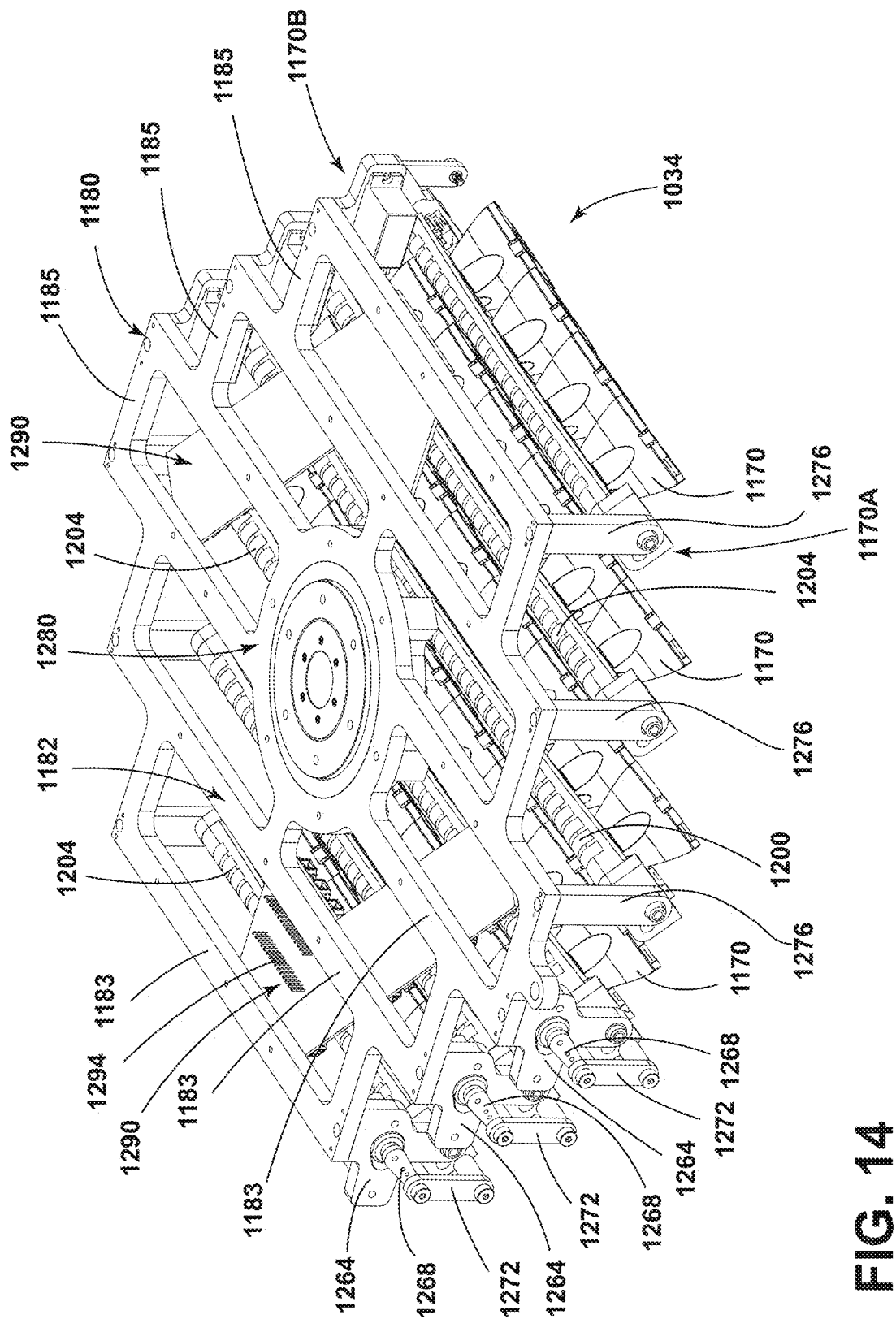
FIG. 14 is a top perspective view of a movable light source illustrated without a housing according to various aspects described herein.

Referring now to FIG. 14, the movable light sources 1034 are illustrated without other components of the light assembly 1014. The illustrative tilt bracket 1182 includes a central, annular portion 1280 interconnected with the rows 1183. The annular portion 1280 may be operably coupled with the belt sprocket 1132 (FIG. 11). Accordingly, the belt sprocket 1132 may drive panning, or rotation, of the tilt bracket 1182. The belt sprocket 1132 may be coupled with the tilt bracket 1182 with any suitable technique, including fasteners and the like.

Additionally, the movable light sources 1034 may include electrical boards 1290 disposed between the tilt bracket 1182 and the LED bulbs 1170, which are configured to electrically couple with the LED bulbs 1170. The illustrative electrical boards 1290 are in the form of printed circuit boards including a plurality of jumper pins 1294. The jumper pins 1294 may be coupled to a power source to provide power to the LED bulbs 1170.

FIG. 15 is a partial exploded view of the movable light sources 1034 illustrating the servo couplings 1260 and servo motors 1300 more clearly. In some aspects, pivot pins 1304 are coupled to the ends 1170A and 1170B of the rows of LED bulbs 1170. The pivot pins 1304 are operably coupled with end caps 1308, which define apertures for receiving the pivot pins 1304. A pivot bushing 1312 may be disposed within the aperture for receiving the pivot pin 1304 to rotatably couple the pivot pin 1304 extending through the end cap 1308 and the servo bracket 1264. Furthermore, the illustrative servo motor 1300 includes a boss 1316 configured to extend through another aperture defined by the servo bracket 1264. One end of the servo arm 1268 is operably coupled to the boss 1316, such that the servo bracket 1264 is disposed between the servo arm 1268 and the servo motor 1300. Another end of the servo arm 1268 is coupled to the servo linkage 1272. The end caps 1308 included in the servo couplings 1260 may additionally include a projection 1320 configured to couple with an aperture defined by the servo linkage 1272. The servo linkage 1272 may be coupled to the projection 1320 with any suitable fastener, such as a shoulder bolt 1324. The servo motor 1300 drives rotation of the servo arm 1268, which translates into movement of the servo linkage 1272 and tilting of the rows of LED bulbs 1170.

Still referring to FIG. 15, the end of the rows of LED bulbs 1170 that opposes the end having the servo couplings 1260 includes the drop brackets 1276. The drop brackets 1276 may define an aperture configured to receive the pivot pins 1304. As such, the end cap 1308 is disposed between the drop brackets 1276 and the pivot pins 1304. The drop brackets 1276 may be coupled to the pivot pins 1304 with any suitable fastener, such as a shoulder bolt 1324.

As can be understood from the description provided herein, the drop brackets 1276 and servo couplings 1260 provide hinge mechanisms to support and provide tilting movement of the rows of LED bulbs 1170. Furthermore, the servo motors 1300, which may be controlled by the controller 82, provide independent control of each of the rows of the LED bulbs 1170.

Each of the light sources 34, 42, 1034, 1042 as well as the gear systems 128, 1128 may be in communication with the controller 82. The controller 82 may be configured to control a direction of the first light 38. Such manipulation of the light assembly 14 may enable the controller 82 to direct the movable light sources 34 to selectively illuminate the operating region 70 or various portions of the medical suite 50 in response to a predetermined desired location. In some implementations, the controller 82 may selectively illuminate the LED bulbs 170, 1170 to narrow/widen the beam of light corresponding to the first light 38. The controller 82 may be configured to selectively illuminate and control individual bulbs 170, 1170 or strips 210, 1210.

The controller 82 may control the motor(s) of the light assemblies 14, 1014 to direct the lighting emissions of the first light 38 to target a desired location in the medical suite 50. A central, or single, controller 82 may control each of the light assemblies 14, 1014 included in the illumination system 10. Alternatively or additionally, the light assemblies 14, 1014 may be in electrical communication with more than one controller 82, which may include on board controllers 82. In specific implementations, the controller 82 may scan the image data from each of the imagers 62 and adjust the orientation of each of the movable light sources 34, 1034 to dynamically control the light in the medical suite 50. Though the imagers 62 are discussed as being incorporated on each of the light assemblies 14, 1014, the illumination system 10 may be configured to capture image data from any location in the medical suite 50. In such embodiments, the central controller 82 may be configured to process the image data from the one or more imagers 62 and communicate control signals for each of the plurality of light assemblies 14, 1014. Optionally, the controller 82 may adjust the orientation of the movable light sources 34, 1034 in response to user input.

Upon signal from a sensor or manual input, the controller 82 may control the movable light sources 34, 1034 forming the first light module and the stationary light sources 42, 1042 forming the second light module to selectively illuminate at a predetermined intensity, or a desired color, such as red. In this way, the light assembly 14 may be beneficial for signaling an emergency. The central controller 82 may be configured to control multiple light assemblies 14, 1014 to work in concert. For example, the controller 82 may sequentially illuminate one or both of the light sources 34, 42, 1034, 1042 of a plurality of light assemblies 14, 1014 to indicate a direction of movement, which may include towards an exit sign.

According to one aspect of the present disclosure, an illumination system includes a light assembly. The light assembly includes a housing having a first zone and a second zone isolated from the first zone. The housing is configured to fit generally flush with a ceiling. A movable light source is positioned within the first zone and is configured to emit a first light. A stationary light source is positioned within the second zone and is configured to emit a second light.

According to another aspect, the first zone is located at a center of the housing and the second zone surrounds the first zone.

According to still another aspect, the housing further comprises a rack at an upper portion thereof, and the movable light source is coupled to the rack via a gear system disposed within the first zone.

According to yet another aspect, the movable light source comprises an array of LED light sources coupled to an arm and the arm is coupled to a belt sprocket assembly configured to rotate at least 360 degrees.

According to another aspect, the belt sprocket assembly is configured to rotate at least 540 degrees.

According to yet another aspect, the array of LED light sources includes at least one of a red, orange, yellow, green, blue, infrared and ultraviolet light.

According to still another aspect, at least one image sensor is configured to collect image data in a field of view, wherein a controller adjusts the orientation of the first light based on the image data.

According to another aspect, at least one image sensor is configured to identify a location of at least one of a marker and a wearable device in a field of view.

According to another aspect, a windowpane is positioned on a bottom surface of the housing, wherein the windowpane comprises at least one of a laminated safety glass and an electrochromic element.

According to another aspect, the movable light source includes a tilt bracket, rows of LED light sources, and servo couplings configured to couple the rows of LED light sources to the tilt bracket.

According to another aspect, the movable light source comprises rows of LED light sources and the rows of LED light sources are independently controlled for tilting movement.

The present disclosure further provides for a method for controlling an illumination system disposed in a housing configured to fit in an opening of a ceiling and comprising an illumination surface configured to align generally flush with the ceiling. The method includes controlling a projection direction of a movable light source emitted from a central portion of light assembly and controlling ambient lighting from a stationary light source distributed about the central portion. The stationary light source is mechanically disconnected from movement of the movable light source. Controlling the movable light source comprises controlling a first rotation of plurality of rows of lights about a first axis configured to rotate the plurality of rows parallel to the illumination surface and controlling a second rotation of a first row of the plurality of rows of lights about a second axis parallel to the illumination surface.

According to some aspects, the method further comprises co-rotating a third rotation of second row of the plurality of rows of lights in connection with the second rotation.

In some aspects, the disclosure provides for a light assembly disposed in a housing. The housing is configured to fit in an opening of a ceiling and comprising an illumination surface configured to align generally flush with the ceiling. The light assembly comprises a first light module centrally suspended from a frame of the housing. The first light module comprises a first plurality of light sources forming a plurality of rows of lights and a first actuator configured to control a first rotation of the plurality of rows of lights about a first axis. The rotation about the first axis rotates the plurality of rows parallel to the illumination surface. The light assembly further comprises a second light module disposed about the first light module. The second light module is fixedly connected to the housing and emits light through the illumination surface.

In some aspects, the first light module further comprises a second actuator in connection with a first row of the plurality of rows of lights. The second actuator is configured to rotate the first row about a second axis parallel to the illumination surface. In some instances, the second actuator may further control a second rotation about the second axis independent of the first rotation controlled by the first actuator. The second axis may also be perpendicular to the first axis.

In some aspects, the plurality of rows of lights may further comprises a second row connected to the first row and configured to co-rotate with the first row in response to the second actuator. The second row may extend along a third axis parallel to the second axis.

In another aspect, the first light module may further comprise a third actuator in connection with a second row of the plurality of rows of lights. The third actuator is configured to rotate the first second row about a third axis parallel to the second axis and controls a third rotation of the second row independent of a second rotation of the first row controlled by the second actuator.

It will be understood by one having ordinary skill in the art that construction of the described disclosure, and other components, is not limited to any specific material. Other exemplary embodiments of the disclosure disclosed herein may be formed from a wide variety of materials unless described otherwise herein.

For purposes of this disclosure, the term "coupled" (in all of its forms: couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system 10 may be varied, and the nature or numeral of adjustment positions provided between the elements may be varied. It should be noted that the elements and/or assemblies of the system 10 may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes, or steps within described processes, may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further, it is to be understood that such concepts are intended to be covered by the following claims, unless these claims, by their language, expressly state otherwise. Further, the claims, as set forth below, are incorporated into and constitute part of this Detailed Description.

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. When the term "about" is used in describing a value or an end-point of a range, the disclosure should be understood to include the specific value or end-point referred to. Whether or not a numerical value or end-point of a range in the specification recites "about," the numerical value or end-point of a range is intended to include two embodiments: one modified by "about," and one not modified by "about." It will be further understood that the end-points of each of the ranges are significant both in relation to the other end-point and independently of the other end-point. The terms "substantial," "substantially," and variations thereof as used herein are intended to note that a described feature is equal or approximately equal to a value or description.

Modifications of the disclosure will occur to those skilled in the art and to those who make or use the disclosure. Therefore, it is understood that the embodiments shown in the drawings and described above are merely for illustrative purposes and not intended to limit the scope of the disclosure, which is defined by the following claims as interpreted according to the principles of patent law, including the Doctrine of Equivalents.

What is claimed is:

1. An illumination system, comprising:
a light assembly comprising a housing comprising a first zone and a second zone mechanically isolated from the first zone, the housing configured to align generally flush with a ceiling;
a movable light source positioned within the first zone and configured to emit a first light; and
a stationary light source positioned about the perimeter within the second zone and configured to emit a second light, wherein the movable light source comprises an array of LED light sources coupled to an arm and the arm is coupled to a belt sprocket assembly configured to rotate at least 360 degrees.

2. The illumination system according to claim 1, wherein the first zone is centrally located within the housing and the second zone substantially surrounds the first zone.

3. The illumination system according to claim 1, wherein the housing further comprises a rack at an upper portion thereof and the movable light source is coupled to the rack via a gear system disposed within the first zone.

4. The illumination system according to claim 1, wherein the belt sprocket assembly is configured to rotate at least 540 degrees.

5. The illumination system according to claim 1, wherein the array of LED light sources includes at least one of a red, orange, yellow, green, blue, infrared and ultraviolet light.

6. The illumination system according to claim 1, further comprising:

at least one image sensor configured to collect image data in a field of view, wherein a controller adjusts the orientation of the first light based on the image data.

7. The illumination system according to claim 1, further comprising:
at least one image sensor configured to identify a location of at least one of a marker and a wearable device in a field of view.

8. The illumination system according to claim 1, further comprising:
a windowpane positioned on a bottom surface of the housing, wherein the windowpane comprises at least one of a laminated safety glass and an electrochromic element.

9. The illumination system according to claim 1, wherein the movable light source comprises:
a tilt bracket;
rows of LED light sources; and
servo couplings configured to couple the rows of LED light sources to the tilt bracket.

10. The illumination system according to claim 1, wherein the movable light source comprises rows of LED light sources and the rows of LED light sources are independently controlled for tilting movement.

11. A method for controlling an illumination system disposed in a housing configured to fit in an opening of a ceiling and comprising an illumination surface configured to align generally flush with the ceiling, the method comprising:
controlling a projection direction of a movable light source emitted from a central portion of the light assembly;
controlling ambient lighting from a stationary light source distributed about the central portion, wherein the stationary light source is mechanically disconnected from movement of the movable light source;
wherein controlling the movable light source comprises:
controlling a first rotation of a plurality of rows of lights about a first axis configured to rotate the plurality of rows parallel to the illumination surface; and
controlling a second rotation of a first row of the plurality of rows of lights about a second axis parallel to the illumination surface.

12. The method according to claim 11, further comprising:
co-rotating a third rotation of a second row of the plurality of rows of lights in connection with the second rotation.

\* \* \* \* \*